US005919782A

United States Patent [19]

Lohray et al.

[11] Patent Number: 5,919,782
[45] Date of Patent: *Jul. 6, 1999

[54] HETEROCYCLIC COMPOUNDS HAVING ANTIDIABETIC, HYPOLIPIDAEMIC, ANTIHYPERTENSIVE PROPERTIES, PROCESS FOR THEIR PREPARATION AND PHARMACEUTICAL COMPOSITIONS CONTAINING THEM

[75] Inventors: Vidya Bhushan Lohray; Braj Bhushan Lohray; Paraselli Bheema Rao; Sekar Reddy Alla; Rajagopalan Ramanujam; Ranjan Chakrabarti, all of Hyderabad, India

[73] Assignees: Dr. Reddy's Research Foundation, Hyderabad, India; Reddy-Cheminor, Inc., Ridgewood, N.J.

[*] Notice: This patent is subject to a terminal disclaimer.

[21] Appl. No.: 08/851,447

[22] Filed: May 5, 1997

Related U.S. Application Data

[63] Continuation-in-part of application No. 08/687,840, Jul. 26, 1996, Pat. No. 5,801,173.

[30] Foreign Application Priority Data

May 6, 1996 [IN] India ......................................... 723/96

[51] Int. Cl.$^6$ ........................ C07D 417/12; A61K 31/425
[52] U.S. Cl. .......................... 514/252; 514/318; 514/342; 514/369; 544/364; 546/194; 546/280; 548/183
[58] Field of Search .......................... 588/183; 544/364; 546/194, 280; 514/252, 318, 342, 369

[56] References Cited

U.S. PATENT DOCUMENTS

| | | | |
|---|---|---|---|
| 4,342,771 | 8/1982 | Schnur | 424/263 |
| 4,367,234 | 1/1983 | Schnur | 424/272 |
| 4,725,610 | 2/1988 | Meguro | 514/369 |
| 4,873,255 | 10/1989 | Yoshioka | 514/369 |
| 5,002,953 | 3/1991 | Hindley | 513/275 |
| 5,036,079 | 7/1991 | Clark | 514/333 |
| 5,037,842 | 8/1991 | Goldstein | 514/375 |
| 5,130,379 | 7/1992 | Clark | 514/333 |
| 5,153,210 | 10/1992 | Ainsworth | 514/369 |
| 5,296,605 | 3/1994 | de Nanteuil | 546/176 |
| 5,330,999 | 7/1994 | de Nanteuil | |
| 5,420,146 | 5/1995 | Malamas | 514/364 |
| 5,468,762 | 11/1995 | Malamas | 514/376 |
| 5,478,851 | 12/1995 | Cantello | 514/369 |
| 5,478,852 | 12/1995 | Olefsky | 514/369 |
| 5,478,853 | 12/1995 | Regnier | 514/369 |
| 5,480,896 | 1/1996 | Malamas | 514/364 |
| 5,498,621 | 3/1996 | Dow | 514/369 |
| 5,521,201 | 5/1996 | Hindley | 514/369 |
| 5,521,202 | 5/1996 | Yano | 514/369 |

FOREIGN PATENT DOCUMENTS

| | | |
|---|---|---|
| 570067 | 5/1992 | Australia . |
| 5355524 | 8/1984 | Estonia . |
| 008203 | 2/1980 | European Pat. Off. . |
| 0139421 | 5/1985 | European Pat. Off. . |
| 155845 | 9/1985 | European Pat. Off. . |
| 0207581 | 1/1987 | European Pat. Off. ...... C07D 417/12 |
| 236624 | 9/1987 | European Pat. Off. . |
| 0306228 | 3/1989 | European Pat. Off. . |
| 0332331 | 9/1989 | European Pat. Off. . |
| 0332332 | 9/1989 | European Pat. Off. . |
| 0337819 | 10/1989 | European Pat. Off. . |
| 0356214 | 2/1990 | European Pat. Off. . |
| 0397453 | 11/1990 | European Pat. Off. . |
| 0415605 | 3/1991 | European Pat. Off. . |
| 0419035 | 3/1991 | European Pat. Off. . |
| 0428312 | 5/1991 | European Pat. Off. . |
| 0439321 | 7/1991 | European Pat. Off. . |
| 0441605 | 8/1991 | European Pat. Off. . |
| 0454501 | 10/1991 | European Pat. Off. . |
| 0528734 | 2/1993 | European Pat. Off. . |
| 0543662 | 5/1993 | European Pat. Off. . |
| 0236624 | 10/1993 | European Pat. Off. ...... C07D 417/38 |
| 590793 | 4/1994 | European Pat. Off. . |
| 0604983 | 7/1994 | European Pat. Off. . |
| 605228 | 7/1994 | European Pat. Off. . |
| 0612743 | 8/1994 | European Pat. Off. . |
| 0643050 | 3/1995 | European Pat. Off. . |
| 645387 | 3/1995 | European Pat. Off. . |
| 0676398 | 10/1995 | European Pat. Off. . |
| 0678511 | 10/1995 | European Pat. Off. . |
| 0708098 | 4/1996 | European Pat. Off. . |
| 0733631 | 9/1996 | European Pat. Off. . |
| 745600 | 12/1996 | European Pat. Off. . |
| 0783888 | 7/1997 | European Pat. Off. . |
| 0787727 | 8/1997 | European Pat. Off. . |
| 62-175458 | 8/1987 | Japan . |
| 6452765 | 2/1989 | Japan . |
| 71-38258 | 5/1995 | Japan . |
| 2558473 | 11/1996 | Japan . |
| 9-12575 | 1/1997 | Japan . |
| 8528633 | 6/1979 | United Kingdom . |
| 9112003 | 8/1991 | WIPO . |
| 9207838 | 5/1992 | WIPO . |
| 9207850 | 5/1992 | WIPO . |

(List continued on next page.)

OTHER PUBLICATIONS

English Translation of JP–A–0912575.
Behavioral Brain Research, 75 (1996) pp. 1–11, Messier, et al.
Chemical Pharamceutical Bulletin, vol. 30 No. 10, 1982 pp. 3580–3600, Taskasi Sohda, et al.
D.A. Clark et al., "Substituted Dihydrobenzeopran . . . ", J. Med. Chem. 1991, 34, 319–325.
R.L. Dow et al., "Benzyloxzolidine–2,4–diones . . . ", J. Med. Chem. 1991, 34, 1538–1544.

(List continued on next page.)

*Primary Examiner*—Robert Gerstl
*Attorney, Agent, or Firm*—Ladas & Parry

[57] ABSTRACT

Novel antidiabetic compounds, their tautomeric forms, their derivatives, their steroisomers, their polymorphs, their pharmaceutically acceptable salts, their pharmaceutically acceptable solvates and pharmaceuticals acceptable compositions containing them; methods for preparing the antidiabetic compounds and their uses.

27 Claims, No Drawings

U.S. PATENT DOCUMENTS

| | | |
|---|---|---|
| 9405659 | 3/1994 | WIPO . |
| 9425026 | 11/1994 | WIPO . |
| 9507697 | 3/1995 | WIPO . |
| 9521608 | 8/1995 | WIPO . |
| 9526347 | 10/1995 | WIPO . |
| 9535108 | 12/1995 | WIPO . |
| 9605186 | 2/1996 | WIPO . |
| 9611196 | 4/1996 | WIPO . |
| 9626207 | 8/1996 | WIPO . |

OTHER PUBLICATIONS

S. W. Goldstein et al., "Hydroxyurea Derivatives . . . ", J. Med. Chem. 1993, 36, 2238–2240.

B. Hulin et al., "Novel Thiazolidine . . . ", J. Med. Chem. 1992, vol. 35 No. 10, 1853–1864.

Journal of Medicinal Chemistry, vol. 37, No. 23, 1994, Barrie, CC. Et al., pp. 3977–3985.

T. Sohda et al., "Studies on Antidiabetic . . . ", J. Med. Chem., 1992, vol. 35, No. 14, 2617–2626.

Khan. A., et al., "Synthesis and Antibacterial Activity of Some New 2–aryloxymethyl–3–substituted–quinazollin–4 (3H)–ones" Pharmazie vol. 43, No. 12. pp. 864–865, 1988.

Chemical Abstracts, vol. 93, No. 17, Oct. 27, 1980, No. 168217.

Shukla, J.S., et al. "Synthesis of 2–phenoxymethyl–3–(2'–pyridyl/ thiazolyl)–4–quinazolones as Possible Antifertility Drugs" Indian Journal Chemical vol. 17B, No. 6, pp. 651–652, Jun. 1979.

Husain, M.I., et al., "Some New 2–aryloxymethyl–3–.alpha.–substituted carboxymethyl–6, 8 substituted 4–quinazolones as Possible Anticonvulsants", Pharmazie, vol. 37, No. 6, 1982, pp. 408–410.

G. De Nanteuil, "Euglygaemic and Biological Activities of Novel Thiazolidine–2, 4–dione Derivatives" Arzneittel Forschung/Drug Design, vol. 45, No. II, 1995, pp. 1176–1181.

Whitcomb, R.W., "Thiazolidinediones", Expert Opinion on Investigational Drugs, vol. 4, No. 12, Dec. 1995, p. 1299–1309.

HETEROCYCLIC COMPOUNDS HAVING ANTIDIABETIC, HYPOLIPIDAEMIC, ANTIHYPERTENSIVE PROPERTIES, PROCESS FOR THEIR PREPARATION AND PHARMACEUTICAL COMPOSITIONS CONTAINING THEM

This application is a continuation-in-part of application application Ser. No. 08/687,840 filed on Jul. 26, 1996, U.S. Pat. No. 5,801,173.

FIELD OF THE INVENTION

The present invention relates to novel antidiabetic compounds, their tautomeric forms, their derivatives, their stereoisomers, their polymorphs, their pharmaceutically acceptable salts, their pharmaceutically acceptable solvates and pharmaceutically acceptable compositions containing them. This invention particularly relates to novel thiazolidinedione derivatives of the general formula (I), their tautomeric forms, their derivatives, their stereoisomers, their polymorphs and their pharmaceutically acceptable salts, pharmaceutically acceptable solvates and pharmaceutical compositions containing them.

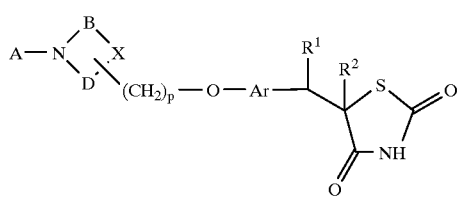

(I)

The present invention also relates to a process for the preparation of the above said novel, thiazolidinedione derivatives, their tautomeric forms, their stereoisomers, their polymorphs, their pharmaceutically acceptable salts, pharmaceutically acceptable solvates, novel intermediates and pharmaceutical compositions containing them.

The thiazolidinedione derivatives of the general formula (I) defined above of the present invention are useful for the treatment and/or prophylaxis of diseases or conditions in which insulin resistance is the underlying pathophysiological mechanism. Examples of these diseases and conditions are type II diabetes, impaired glucose tolerance, dyslipidaemia, hypertension, coronary heart disease and other cardiovascular disorders including atherosclerosis. The thiazolidinedione derivatives of the formula (I) are useful for the treatment of insulin resistance associated with obesity and psoriasis. The thiazolidinedione derivatives of the formula (I) can also be used to treat diabetic complications and can be used for treatment and/or prophylaxis of other diseases and conditions such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia.

BACKGROUND OF THE INVENTION

Insulin resistance is the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and is associated with a variety of abnormalities including obesity, hypertension, hyperlipidemia (J. Clin. Invest., (1985) 75: 809–817; N. Engl. J. Med. (1987) 317: 350–357; J. Clin. Endocrinol. Metab., (1988) 66: 580–583; J. Clin. Invest., (1975) 68: 957–969) and other renal complications (See Patent Application No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X. In addition, polycystic ovarian syndrome (Patent Application No. WO 95/07697), psoriasis (Patent Application No. WO 95/35108), dementia (Behavioral Brain Research (1996) 75: 1–11) etc. may also have insulin resistance as a central pathogenic feature.

A number of molecular defects have been associated with insulin resistance. These include reduced expression of insulin receptors on the plasma membrane of insulin responsive cells and alterations in the signal transduction pathways that become activated after insulin binds to its receptor including glucose transport and glycogen synthesis.

Since defective insulin action is thought to be more important than failure of insulin secretion in the development of non-insulin dependent diabetes mellitus and other related complications, this raises doubts about the intrinsic suitability of antidiabetic treatment that is based entirely upon stimulation of insulin release. Recently, Takeda has developed a new class of compounds which are the derivatives of 5-(4-alkoxybenzyl)-2,4-thiazolidinediones of the formula (II) (Ref. Chem. Pharm. Bull. 1982, 30, 3580–3600). In the formula (II), V represents substituted or unsubstituted divalent aromatic group and U represents various groups which have been reported in various patent documents.

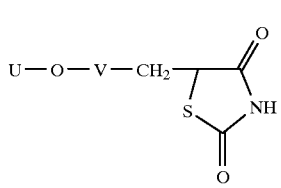

(II)

By way of examples, U may represent the following groups:

(i) a group of the formula (IIa) where $R^1$ is hydrogen or hydrocarbon residue or heterocyclic residue which may each be substituted, $R^2$ is hydrogen or a lower alkyl which may be substituted by hydroxy group, X is an oxygen or sulphur atom, Z is a hydroxylated methylene or a carbonyl, m is 0 or 1, n is an integer of 1–3. These compounds have been disclosed in the European Patent Application No. 0 177 353

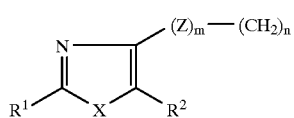

(IIa)

An example of these compounds is shown in formula (IIb)

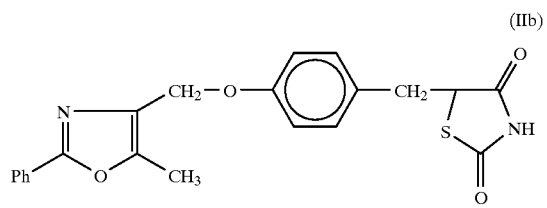
(IIb)

An example of this compound is shown in formula (IIf)

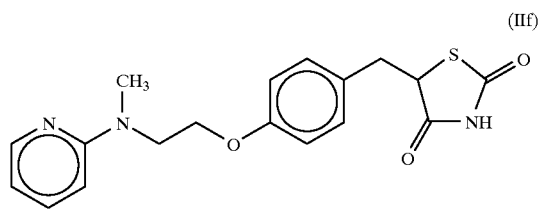
(IIf)

(ii) a group of the formula (IIc) wherein $R^1$ and $R^2$ are the same or different and each represents hydrogen or $C_1$–$C_5$ alkyl, $R^3$ represents hydrogen, acyl group, a ($C_1$–$C_6$) alkoxycarbonyl group or aralkyloxycarbonyl group, $R^4$ and $R^5$ are same or different and each represent hydrogen, $C_1$–$C_5$ alkyl or $C_1$–$C_5$ alkoxy or $R^4$, $R^5$ together represent $C_1$–$C_4$ alkenedioxy group, n is 1, 2, or 3, W represents $CH_2$, CO, $CHOR^6$ group in which $R^6$ represents any one of the items or groups defined for $R^3$ and may be the same or different from $R^3$. These compounds are disclosed in the European Patent Application No. 0 139 421.

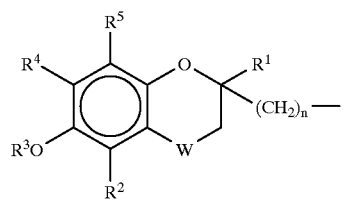
(IIc)

An example of these compounds is shown in (IId)

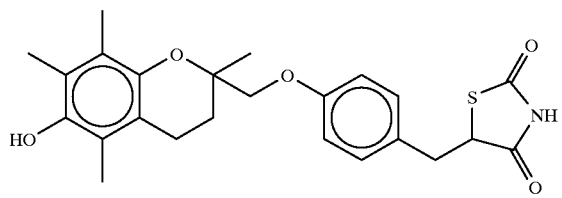
(IId)

iii) A group of formula (IIe) where $A^1$ represents substituted or unsubstituted aromatic heterocyclic group, $R^1$ represents a hydrogen atom, alkyl group, acyl group, an aralkyl group wherein the aryl moiety may be substituted or unsubstituted, or a substituted or unsubstituted aryl group, n represents an integer in the range from 2 to 6. These compounds are disclosed in European Patent No. 0 306 228.

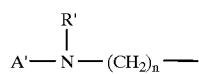
(IIe)

iv) A group of formula (IIg) where Y represents N or $CR^5$, $R^1$, $R^2$, $R^3$, $R^4$ and $R^5$ represents hydrogen, halogen, alkyl and the like and $R^6$ represents hydrogen, alkyl, aryl and the like, n represents an integer of 0 to 3. These compounds are disclosed in European Patent Application No. 0 604 983.

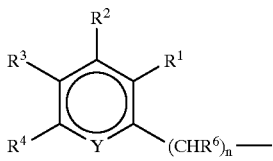
(IIg)

An example of this compound is shown in formula (IIh)

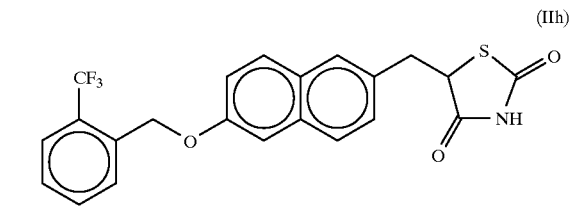
(IIh)

v) A group of formula (IIi a–d) where $R^1$ represents hydrogen atom, halogen, linear or branched ($C_1$–$C_6$)alkyl, ($C_1$–$C_6$)alkoxy, trifluoromethyl or cyano groups and X represents S, O or NR where R=H or ($C_1$–$C_6$)alkyl group. These compounds are disclosed in European Patent Application No. 0 528 734.

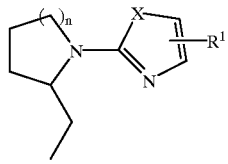
(IIi a)

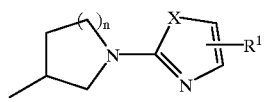
(IIi b)

-continued

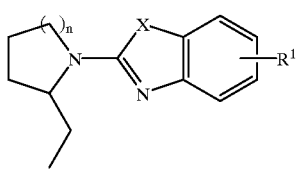

(IIi c)

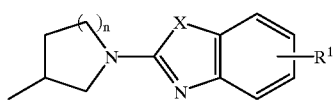

(IIi d)

An example of this class of compound is shown in formula (IIj)

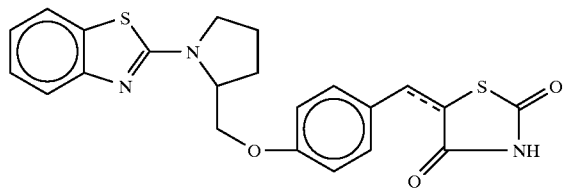

(IIj)

Some of the above referred hitherto known antidiabetic compounds seem to possess bone marrow depression, liver and cardiac toxicities or modest potency and consequently, their regular use for the treatment and control of diabetes is becoming limited and restricted.

SUMMARY OF THE INVENTION

With an objective of developing new compounds for the treatment of type II diabetes [non-insulin-dependent-diabetes mellitus (NIDDM)] which could be more potent at relatively lower doses and having better efficacy with lower toxicity, we focused our research efforts in a direction of incorporating safety and to have better efficacy, which has resulted in the development of novel thiazolidinedione derivatives having the general formula (I) as defined above.

The main objective of the present invention is therefore, to provide novel thiazolidinedione derivatives, their tautomeric forms, their stereoisomers, their polymorphs, their pharmaceutically, acceptable salts, their pharmaceutically acceptable solvates and pharmaceutical compositions containing them, or their mixtures.

Another objective of the present invention is to provide novel thiazolidinedione derivatives, their tautomeric forms, their stereoisomers, their polymorphs, their pharmaceutically acceptable salts, their pharmaceutically acceptable solvates and pharmaceutical compositions containing them or their mixtures having enhanced activities, no toxic effect or reduced toxic effect.

Yet another objective of the present invention is to produce a process for the preparation of novel thiazolidinediones of the formula (I) as defined above, their tautomeric forms, their stereoisomers, their polymorphs, their pharmaceutically acceptable salts and their pharmaceutically acceptable solvates.

Still another objective of the present invention is to provide pharmaceutical compositions containing compounds of the general formula (I), their tautomers, their stereoisomers, their polymorphs, their salts, solvates or their mixtures in combination with suitable carriers, solvents, diluents and other media normally employed in preparing such compositions

DETAILED DESCRIPTION OF THE INVENTION

Thiazolidinedione derivatives of the present invention have the general formula (I)

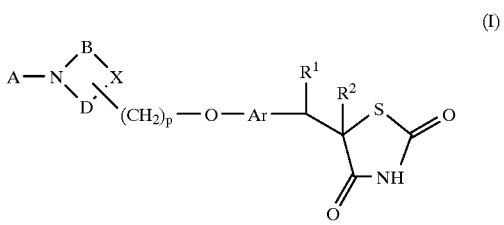

(I)

In the above formula (I), A represents a substituted or unsubstituted aromatic group, a substituted or unsubstituted five membered heterocyclic group with one hetero atom selected from nitrogen, oxygen or sulfur, which is single or fused or a substituted or unsubstituted six membered heterocyclic group with one or more nitrogen atoms, which is single or fused, which may or may not contain one or more oxo group on the ring, B and D represent substituted or unsubstituted hydrocarbon linking group between N and X which may or may not contain one or more double bonds, X represents either a $CH_2$ group or a hetero atom selected from the group of nitrogen, oxygen or sulfur, Ar represents an optionally substituted divalent aromatic or heterocyclic group, $R^1$ and $R^2$ can be the same or different and represent hydrogen atom, lower alkyl, halogen, alkoxy or hydroxy groups or $R^1$ and $R^2$ together represent a bond and p is an integer ranging from 0–4.

A may be a six membered heterocyclic group which contains 1–3 nitrogen atoms and A may be a single or fused ring which is substituted or unsubstituted and may contain up to 3 oxo groups.

Suitable aromatic groups represented by A include phenyl, naphthyl, phenanthryl, preferably, phenyl and naphthyl group, suitable heterocyclic groups represented by A include furyl, pyrrolyl, thienyl, pyridyl, quinolyl, 4-pyridone-2-yl, pyrimidyl, 4-pyrimidone-2-yl, pyridazyl, and 3-pyridazone-2-yl groups, pthalazinyl, phthalazinonyl, quinoxalinyl, quinoxalonyl, quinazolinyl, quinazolinonyl, azaindolyl, naphtharidinyl, carbazolyl, indolyl, benzofuranyl, pyrimidonyl, and the like.

Preferred groups represented by A include pyridyl, quinolyl, indolyl, benzofuranyl, pyrimidonyl, quinazolinonyl groups.

More preferred groups represented by A include pyridyl and quinolyl groups. One or more of the suitable substituents on the aromatic and heterocyclic group represented by A include hydroxy, amino group, halogen atoms such as chlorine, fluorine, bromine, or iodine, substituted or unsubstituted ($C_1$–$C_{12}$)alkyl group, especially, linear or branched ($C_1$–$C_6$)alkyl group, such as methyl, ethyl, n-propyl, isopropyl, n-butyl, iso-butyl, t-butyl, pentyl, hexyl and the like; cycloalkyl group such as cyclopropyl, cyclobutyl, cyclopentyl, cyclohexyl and the like; cycloalkyloxy group such as cyclopropyloxy, cyclobutyloxy, cyclopentyloxy, cyclohexyloxy and the like; aryl group such as phenyl or naphthyl, the aryl group may be substituted; aralkyl such as benzyl or phenethyl, the aralkyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuranyl and the like, the heteroaryl group may be substituted; heterocyclyl groups such as aziridinyl, pyrrolidinyl, morpholinyl, piperidinyl, piperazinyl and the like, the heterocyclyl group may be substituted; aryloxy such as phenoxy, naphthyloxy, the aryloxy group may be substituted; alkoxycarbonyl such as methoxycarbonyl or ethoxycarbonyl; aryloxycarbonyl group such as optionally substituted phenoxycarbonyl; arylamino group such as $HNC_6H_5$, amino($C_1$–$C_6$)alkyl; hydroxy($C_1$–$C_6$) alkyl; ($C_1$–$C_6$)alkoxy; thio($C_1$–$C_6$)alkyl; ($C_1$–$C_6$) alkylthio; acyl group such as acetyl, propionyl or benzoyl, the acyl group may be substituted; acylamino groups such as $NHCOCH_3$, $NHCOC_2H_5$, $NHCOC_3H_7$, $NHCOC_6H_5$, aralkoxycarbonylamino group such as $NHCOOCH_2C_6H_5$, alkoxycarbonylamino group such as $NHCOOC_2H_5$, $NHCOOCH_3$ and the like; carboxylic acid or its derivatives such as amides, like $CONH_2$, CONHMe, $CONMe_2$, CONHEt, $CONEt_2$, CONHPh and the like, the carboxylic acid derivatives may be substituted; acyloxy group such as OOCMe, OOCEt, OOCPh and the like which may optionally be substituted; sulfonic acid or its derivatives such as $SO_2NH_2$, $SO_2NHMe$, $SO_2NMe_2$, $SO_2NHCF_3$, $SO_2NHPh$ and the like; the sulfonic acid derivatives may be substituted.

All of the suitable substituents on group A may be substituted or unsubstituted.

When the substituents are further substituted, the substituents selected are from the same groups as those groups that substitute A and may be selected from halogen, hydroxy, or nitro, or optionally substituted groups selected from alkyl, cycloalkyl, alkoxy, cycloalkoxy, aryl, aralkyl, heterocyclyl, heteroaryl, heteroaralkyl, acyl, acyloxy, hydroxyalkyl, amino, acylamino, arylamino, aminoalkyl, aryloxy, alkoxycarbonyl, alkylamino, alkoxyalkyl, alkylthio, thioalkyl groups, carboxylic acid or its derivatives, or sulfonic acid or its derivatives.

The substituents on the adjacent carbon atoms on the group represented by A along with the carbon atoms to which they are attached may also form a substituted or unsubstituted, aromatic, saturated or unsaturated 5–7 membered cyclic structure which may be carbocyclic or heterocyclic wherein one or more hetero atoms are selected from N, O, and S, such as phenyl, naphthyl, thienyl, furyl, oxazolyl, thiazolyl, furyl, imidazolyl, azacyclobutyl, isoxazolyl, azepinyl and the like, preferably, phenyl, furyl and imidazolyl groups. The substituents on such cyclic structure may be selected from the same group that may substitute the aromatic and heterocyclic group represented by A.

Suitable hydrocarbon linking group between N and X represented by B may contain 1–4 carbon atoms, 1–2 being preferred and suitable linking group between N and X represented by D may represent either a bond or contain 1–4 carbon atoms, 1–2 being preferred. The compounds according to formula (I) always have a linking group B and a linking group D. The linking group D having no carbon atom means that the linking group D represents a bond. B and D may contain no double bond or contain one to two double bonds, no double bond or one double bond being preferred. The substituents on the B and D include hydroxy; amino groups; halogen such as chlorine, bromine, or iodine; optionally substituted linear or branched ($C_1$–$C_{12}$)alkyl, especially ($C_1$–$C_6$)alkyl group such as methyl, hydroxymethyl, aminomethyl, methoxymethyl, trifluoromethyl, ethyl, isopropyl, hexyl etc; ($C_3$–$C_6$) cycloalkyl groups such as cyclopropyl, fluorocyclopropyl, cyclobutyl, cyclopentyl, fluorocyclopentyl, cyclohexyl, fluorocyclohexyl and the like; ($C_1$–$C_6$)alkoxy, ($C_3$–$C_6$) cycloalkoxy, aryl such as phenyl; heterocyclic groups such as furyl, thienyl and the like; ($C_2$–$C_6$) acyl, ($C_2$–$C_6$)acyloxy, hydroxy($C_1$–$C_6$)alkyl, amino($C_1$–$C_6$)alkyl, mono or di($C_1$–$C_6$)alkylamino, cyclo($C_3$–$C_5$)alkylamino groups; two substituents together with the adjacent carbon atoms to which they are attached may form a substituted or unsubstituted 5–7 membered cyclic structure which may or may not contain one or more hetero atoms selected from N, O, and S; such cyclic structures may or may not contain one or more double bonds. Preferred ring structures include phenyl, naphthyl, pyridyl, thienyl, furyl, oxazolyl, thiazolyl, furyl, isoxazolyl, azepinyl and the like. The substituents on such cyclic structure may be selected from the same group that may substitute the aromatic or heterocyclic group represented by A.

Suitable X includes $CH_2$, O, N or S group, preferably $CH_2$ and O. Preferred ring structures comprising a nitrogen atom, linking groups represented by B and D, and X are pyrrolidinyl, piperidinyl, piperazinyl, aziridinyl and morpholinyl groups.

It is more preferred that the ring structures comprising a nitrogen atom, linking groups represented by B and D, and X are a pyrrolidinyl group, morpholinyl or aziridinyl group.

The group represented by Ar includes divalent phenylene, naphthylene, pyridyl, quinolinyl, benzofuranyl, benzoxazolyl, benzothiazolyl, indolyl, indolinyl, azaindolyl, azaindolinyl, indenyl, pyrazolyl and the like. The substituents on the group represented by Ar include linear or branched optionally halogenated ($C_1$–$C_6$)alkyl and optionally halogenated ($C_1$–$C_3$)alkoxy, halogen, acyl, amino, acylamino, thio, carboxylic and sulfonic acids and their derivatives.

It is more preferred that Ar represents substituted or unsubstituted divalent phenylene, naphthylene, benzofuranyl, indolyl, indolinyl, quinolinyl, azaindolyl, azaindolinyl, benzothiazolyl or benzoxazolyl groups.

It is still more preferred that Ar is represented by divalent phenylene or naphthylene, which may be optionally substituted by methyl, halomethyl, methoxy or halomethoxy groups.

Suitable $R^1$ and $R^2$ include hydrogen, lower alkyl groups such as methyl, ethyl or propyl; halogen atoms such as fluorine, chlorine, bromine or iodine; ($C_1$–$C_3$)alkoxy, hydroxy or $R^1$ and $R^2$ together represent a bond; preferably both $R^1$ and $R^2$ are hydrogen or together represent a bond.

Suitable p is an integer ranging from 0–4, preferably 0–2. When p is zero, $(CH_2)_p$ represents a bond; the ring structure comprising N, X and the linking groups B and D is directly linked to oxygen atom.

Pharmaceutically acceptable salts forming part of this invention include salts of the thiazolidinedione moiety such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, salts of carboxy group wherever appropriate, such as aluminum, alkali metal salts, alkaline earth metal salts, ammonium or substituted ammonium salts. Salts may include acid addition salts which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like.

Pharmaceutically acceptable solvates may be hydrates or comprising other solvents of crystallization such as alcohols.

Particularly useful compounds according to the invention include:

5-[4-[[1-(Pyridin-2-yl)-(2S)-pyrrolidin-2-yl]methoxy] phenyl methylene]thiazolidine-2,4-dione;

5-[4-[[1-(Pyridin-2-yl)-(2R)-pyrrolidin-2-yl]methoxy] phenyl methylene]thiazolidine-2,4-dione;

5-[4-[[1-(Pyridin-2-yl)-(2S)-pyrrolidin-2-yl]methoxy] phenyl methyl]thiazolidine-2,4-dione;

5-[4-[[1-(Pyridin-2-yl)-(2R)-pyrrolidin-2-yl]methoxy] phenyl methyl]thiazolidine-2,4-dione;

5-[4-[[1-(Pyridin-2-yl)piperidin-4-yloxy]phenyl methylene]thiazolidine-2,4-dione;

5-[4-[[1-(Pyridin-2-yl)piperidin-4-yl]methoxy]phenyl methylene]thiazolidine-2,4-dione;

5-[4-[2-[4-(Pyridin-2-yl)piperazin-1-yl]ethoxy]phenyl methylene]thiazolidine-2,4-dione;

5-[4-[[1-(Pyridin-2-yl)-(2S)-pyrrolidin-2-yl]methoxy] phenyl methylene]thiazolidine-2,4-dione, maleic acid salt;

5-[4-[[1-(Pyridin-2-yl)-(2R)-pyrrolidin-2-yl]methoxy] phenyl methylene]thiazolidine-2,4-dione, maleic acid salt;

5-[4-[[1-(Pyridin-2-yl)-(2S)-pyrrolidin-2-yl]methoxy] phenyl methylene]thiazolidine-2,4-dione, hydrochloride salt;

5-[4-[[1-(Pyridin-2-yl)-(2R)-pyrrolidin-2-yl]methoxy] phenyl methylene]thiazolidine-2,4-dione, hydrochloride salt;

5-[4-[[1-(Pyridin-2-yl)-(2S)-pyrrolidin-2-yl]methoxy] phenyl methylene]thiazolidine-2,4-dione, sodium salt;

5-[4-[[1-(Pyridin-2-yl)-(2R)-pyrrolidin-2-yl]methoxy] phenyl methylene]thiazolidine-2,4-dione, sodium salt;

5-[4-[[1-(Pyridin-2-yl)-(2S)-pyrrolidin-2-yl]methoxy] phenyl methyl]thiazolidine-2,4-dione, maleic acid salt;

5-[4-[[1-(Pyridin-2-yl)-(2R)-pyrrolidin-2-yl]methoxy] phenyl methyl]thiazolidine-2,4-dione, maleic acid salt;

5-[4-[[1-(Pyridin-2-yl)-(2S)-pyrrolidin-2-yl]methoxy] phenyl methyl]thiazolidine-2,4-dione, sodium salt;

5-[4-[[1-(Pyridin-2-yl)-(2R)-pyrrolidin-2-yl]methoxy] phenyl methyl]thiazolidine-2,4-dione, sodium salt;

5-[4-[[1-(Quinolin-2-yl)-(2S)-pyrrolidin-2-yl]methoxy] phenyl methylene]thiazolidine-2,4-dione;

5-[4-[[1-(Quinolin-2-yl)-(2R)-pyrrolidin-2-yl]methoxy] phenyl methylene]thiazolidine-2,4-dione;

5-[4-[[1-(Quinolin-2-yl)-(2S)-pyrrolidin-2-yl]methoxy] phenyl methyl]thiazolidine-2,4-dione;

5-[4-[[1-(Quinolin-2-yl)-(2R)-pyrrolidin-2-yl]methoxy] phenyl methyl]thiazolidine-2,4-dione;

5-[4-[[1-(Quinolin-2-yl)-(2S)-pyrrolidin-2-yl]methoxy] phenyl methyl]thiazolidine-2,4-dione, maleic acid salt;

5-[4-[[1-(Quinolin-2-yl)-(2R)-pyrrolidin-2-yl]methoxy] phenyl methyl]thiazolidine-2,4-dione, maleic acid salt;

5-[4-[[1-(Quinolin-2-yl)-(2S)-pyrrolidin-2-yl]methoxy] phenyl methyl]thiazolidine-2,4-dione, hydrochloride;

5-[4-[[1-(Quinolin-2-yl)-(2R)-pyrrolidin-2-yl]methoxy] phenyl methyl]thiazolidine-2,4-dione, hydrochloride;

5-[4-[[1-(Quinolin-2-yl)-(2S)-pyrrolidin-2-yl]methoxy] phenyl methyl]thiazolidine-2,4-dione, sodium salt;

5-[4-[[1-(Quinolin-2-yl)-(2R)-pyrrolidin-2-yl]methoxy] phenyl methyl]thiazolidine-2,4-dione, sodium salt;

5-[4-[[1-(Lepidin-2-yl)-(2S)-pyrrolidin-2-yl]methoxy] phenyl methylene]thiazolidine-2,4-dione;

5-[4-[[1-(Lepidin-2-yl)-(2R)-pyrrolidin-2-yl]methoxy] phenyl methylene]thiazolidine-2,4-dione;

5-[4-[[1-(Lepidin-2-yl)-(2S)-pyrrolidin-2-yl]methoxy] phenyl methyl]thiazolidine-2,4-dione;

5-[4-[[1-(Lepidin-2-yl)-(2R)-pyrrolidin-2-yl]methoxy] phenyl methyl]thiazolidine-2,4-dione;

5-[4-[[1-(Lepidin-2-yl)-(2S)-pyrrolidin-2-yl]methoxy] phenyl methyl]thiazolidine-2,4-dione, maleic acid salt;

5-[4-[[1-(Lepidin-2-yl)-(2R)-pyrrolidin-2-yl]methoxy] phenyl methyl]thiazolidine-2,4-dione, maleic acid salt;

5-[4-[[1-(Lepidin-2-yl)-(2S)-pyrrolidin-2-yl]methoxy] phenyl methyl]thiazolidine-2,4-dione, hydrochloride salt;

5-[4-[[1-(Lepidin-2-yl)-(2R)-pyrrolidin-2-yl]methoxy] phenyl methyl]thiazolidine-2,4-dione, hydrochloride salt;

5-[4-[[1-(Lepidin-2-yl)-(2S)-pyrrolidin-2-yl]methoxy] phenyl methyl]thiazolidine-2,4-dione, sodium salt;

5-[4-[[1-(Lepidin-2-yl)-(2R)-pyrrolidin-2-yl]methoxy] phenyl methyl]thiazolidine-2,4-dione, sodium salt;

5-[4-[[1-(Pyridin-2-yl)pyrrolidin-3-yloxy]phenyl methylene]thiazolidine-2,4-dione;

5-[4-[[1-(Pyridin-2-yl)-(3S)-pyrrolidin-3-yloxy]phenyl methylene]thiazolidine-2,4-dione and its salts;

5-[4-[[1-(Pyridin-2-yl)-(3R)-pyrrolidin-3-yloxy]phenyl methylene]thiazolidine-2,4-dione and its salts;

5-[4-[[1-(Pyridin-2-yl)pyrrolidin-3-yloxy]phenyl methylene]thiazolidine-2,4-dione, maleic acid salt;

5-[4-[[1-(Pyridin-2-yl)pyrrolidin-3-yloxy]phenyl methylene]thiazolidine-2,4-dione, hydrochloride salt;

5-[4-[[1-(Pyridin-2-yl)pyrrolidin-3-yloxy]phenyl methyl] thiazolidine-2,4-dione;

5-[4-[[1-(Pyridin-2-yl)-(3S)-pyrrolidin-3-yloxy]phenyl methyl]thiazolidine-2,4-dione and its salts;

5-[4-[[1-(Pyridin-2-yl)-(3R)-pyrrolidin-3-yloxy]phenyl methyl]thiazolidine-2,4-dione and its salts;

5-[4-[[4-(Pyridin-2-yl)morpholin-2-yl]methoxy]phenyl methylene]thiazolidine-2,4-dione and its salts;

5-[4-[[4-(Pyridin-2-yl)-(2S)-morpholin-2-yl]methoxy] phenyl methylene]thiazolidine-2,4-dione and its salts;

5-[4-[[4-(Pyridin-2-yl)-(2R)-morpholin-2-yl]methoxy] phenyl methylene]thiazolidine-2,4-dione and its salts;

5-[4-[[4-(Pyridin-2-yl)morpholin-2-yl]methoxy]phenyl methyl]thiazolidine-2,4-dione and its salts;

5-[4-[[4-(Pyridin-2-yl)-(2S)-morpholin-2-yl]methoxy] phenyl methyl]thiazolidine-2,4-dione and its salts;

5-[4-[[4-(Pyridin-2-yl)-(2R)-morpholin-2-yl]methoxy] phenyl methyl]thiazolidine-2,4-dione;

5-[4-[[4-(Pyridin-2-yl)morpholin-2yl]methoxy]phenyl methyl]thiazolidine-2,4-dione, sodium salt;

5-[4-[[4-(Pyridin-2-yl)-(2S)-morpholin-2yl]methoxy] phenyl methyl]thiazolidine-2,4-dione, sodium salt;

5-[4-[[4-(Pyridin-2-yl)-(2R)-morpholin-2yl]methoxy] phenyl methyl]thiazolidine-2,4-dione, sodium salt;

5-[4-[[4-(Pyridin-2-yl)aziridin-2-yl]methoxy]phenyl methylene]thiazolidine-2,4-dione;

5-[4-[[4-(Pyridin-2-yl)-(2S)-aziridin-2-yl]methoxy] phenyl methylene]thiazolidine-2,4-dione;

5-[4-[[4-(Pyridin-2-yl)-(2R)-aziridin-2-yl]methoxy] phenyl methylene]thiazolidine-2,4-dione;

5-[4-[[4-(Pyridin-2-yl)aziridin-2-yl]methoxy]phenyl methyl]thiazolidine-2,4-dione;

5-[4-[[4-(Pyridin-2-yl)-(2S)-aziridin-2-yl]methoxy] phenyl methyl]thiazolidine-2,4-dione;

5-[4-[[4-(Pyridin-2-yl)-(2R)-aziridin-2-yl]methoxy] phenyl methyl]thiazolidine-2,4-dione;

5-[4-[[4-(Quinolin-2-yl)aziridin-2-yl]methoxy]phenyl methylene]thiazolidine-2,4-dione;

5-[4-[[4-(Quinolin-2-yl)-(2S)-aziridin-2-yl]methoxy] phenyl methylene]thiazolidine-2,4-dione;

5-[4-[[4-(Quinolin-2-yl)-(2R)-aziridin-2-yl]methoxy] phenyl methylene]thiazolidine-2,4-dione;

5-[4-[[4-(Quinolin-2-yl)aziridin-2-yl]methoxy]phenyl methyl]thiazolidine-2,4-dione;

5-[4-[[4-(Quinolin-2-yl)-(2S)-aziridin-2-yl]methoxy] phenyl methyl]thiazolidine-2,4-dione; and 5-[4-[[4-(Quinolin-2-yl)-(2R)-aziridin-2-yl]methoxy] phenyl methyl]thiazolidine-2,4-dione.

According to a feature of the present invention, there is provided a process for the preparation of novel thiazolidinedione derivatives of formula (I), their stereoisomers, their polymorphs, their tautomeric forms, their pharmaceutically acceptable salts, their pharmaceutically acceptable solvates, which comprises.

(a) reacting a compound of general formula (III)

A—L¹                 (III)

where A is as defined above and L¹ is a halogen atom such as chlorine, bromine or iodine; a thioalkyl group such as thiomethyl group, or a group capable of coupling with an amine nitrogen atom, with a compound of general formula (IV)

(IV)

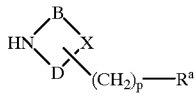

where B, D, X and p are as defined earlier and $R^a$ is a hydroxy group or a group which can be converted to a hydroxy group or a leaving group such as OMs, OTs, Cl, Br or I, by conventional methods, to yield a compound of general formula (V)

(V)

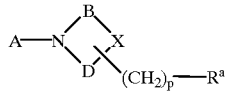

where A, B, D, $R^a$, X and p are as defined earlier.

The reaction of compound of general formula (III) with a compound of general formula (IV) to yield a compound of general formula (V) may be carried out in neat or in the presence of solvents such as DMF, DMSO, acetone, CH₃CN, THF, pyridine or ethanol. Mixture of solvents may be used. The reaction may be carried out in an inert atmosphere. The inert atmosphere may be maintained by using inert gases such as N₂, Ar or He. The reaction may be effected in the presence of a base such as K₂CO₃, Na₂CO₃, KOH, NaOH, NaH and the like or mixture thereof. The amount of base may range from 1 to 20 equivalents, preferably 1 to 10 equivalents. The reaction may be carried out at a temperature in the range 20° C. to 180° C., preferably at a temperature in the range 50° C.–150° C. Duration of the reaction may range from 1 to 48 hours, preferably from 1 to 12 hours. In the reaction, the ratio of the compound of general formula (III) and (IV) may range from 1 to 20 equivalents, preferably from 1 to 5 equivalents.

(b) reacting the compound of general formula (V) where $R^a$ is a hydroxy group with a compound of general formula (VI)

R^b—Ar—CHO            (VI)

where Ar is as defined earlier and $R^b$ is a halogen atom such as chlorine or fluorine, or $R^b$ is a hydroxy group to yield a compound of general formula (VII)

(VII)

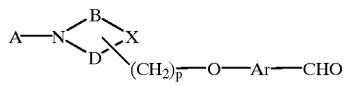

where A, B, D, X, Ar and p are as defined earlier.

The reaction of compound of general formula (V) where $R^a$ is a hydroxy group with the compound of general formula (VI) where $R^b$ is a halogen atom to give a compound of general formula (VII) may be carried out in the presence of solvents such as THF, DMF, DMSO, DME and the like or a mixture thereof. The reaction may be carried out in an inert atmosphere. The inert atmosphere may be maintained by using inert gases such as N₂, Ar, or He. The reaction may be effected in the presence of a base such as K₂CO₃, Na₂CO₃, or NaH. Mixture of bases may be used. The reaction temperature may range from 20° C. to 120° C., preferably at a temperature in the range of 30° C. to 80° C. The duration of the reaction may range from 1 to 24 hours, preferably from 2 to 12 hours.

The reaction of compound of general formula (V) where $R^a$ is a hydroxy group with the compound of general formula (VI) where $R^b$ is a hydroxy group may be carried out using suitable coupling agents such as dicyclohexyl urea, triarylphosphine/dialkylazodicarboxylate such as PPh₃/DEAD and the like. The reaction may be carried out in the presence of solvents such as THF, DME, CH₂Cl₂, CHCl₃, toluene, acetonitrile, carbontetrachloride and the like or a mixture thereof The reaction may be carried out in an inert atmosphere. The inert atmosphere may be maintained by using inert gases such as N₂, Ar, or He. The reaction may be effected in the presence of DMAP-HOBT and they may be used in the range of 0.05 to 2 equivalents, preferably 0.25 to 1 equivalents. The reaction temperature may be in the range of 0° C. to 100° C., preferably at a temperature in the range of 20° C. to 50° C. The duration of the reaction may range from 0.5 to 24 hours, preferably from 6 to 12 hours.

(c) reacting the compound of general formula (VII) with 2,4-thiazolidinedione to yield a compound of general formula (VIII)

(VIII)

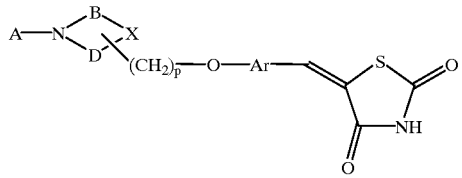

where A, B, D, X, Ar, p are as defined earlier and removing the water formed during the reaction by conventional methods.

The reaction between the compound of general formula (VII) with 2,4-thiazolidinedione to give a compound of general formula (VIII) in step (c) may be carried out neat in the presence of sodium acetate or in the presence of a solvent such as benzene, toluene, methoxyethanol or a mixture thereof. The reaction temperature may range from 80° C. to 140° C. depending upon the solvents employed. A suitable catalyst such as piperidinium acetate or benzoate, or sodium acetate may also be employed. The water produced in the reaction may be removed, for example, by using Dean Stark water separator or by using water absorbing agents like molecular sieves etc.

And if desired, (d) reducing the compound of general formula (VIII) obtained in step (c) by known methods, to obtain the compound of general formula (IX)

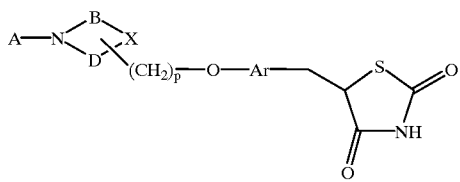

(IX)

where A, B, D, X, Ar and p are as defined earlier.

The reduction of compound of the formula (VIII) obtained in step (c) to yield a compound of the general formula (IX) may be carried out in the presence of gaseous hydrogen and a catalyst such as Pd/C, Rh/C, Pt/C, and the like. Mixtures of catalysts may be used. The reaction may also be conducted in the presence of solvents such as dioxane, acetic acid, ethyl acetate and the like. Mixtures of solvents may be used. A pressure between atmospheric pressure and 80 psi may be employed. The catalyst may be 5–10% Pd/C and the amount of catalyst used may range from 50–300% w/w. The reaction may also be carried out by employing metal solvent reduction such as magnesium in methanol or sodium amalgam in methanol. The reaction may also be carried out with alkali metal borohydrides such as LiBH$_4$, NaBH$_4$, KBH$_4$ and the like in the presence of cobalt salt such as CoCl$_2$ and ligands, preferably bidentated ligands such as 2,2'-bipyridyl, 1,10-phenanthroline, bisoximes and the like.

And if desired, (e) resolving the compound of general formula (VIII) and of general formula (IX) into their stereoisomers and if desired, (f) converting the compound of the general formula (VIII) and compound of general formula (IX) obtained in steps (c) and (d) respectively or the resolved stereoisomers thereof into their pharmaceutically acceptable salts, or their pharmaceutically acceptable solvates by conventional methods.

In an embodiment of the invention, the compound of general formula (VII) can be prepared by converting the compound of general formula (V) to a compound of general formula (X)

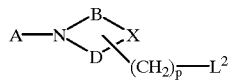

(X)

where A, B, D, X and p are as defined earlier and L$^2$ is a leaving group such as halide group like chloride, bromide or iodide, or methanesulfonate, p-toluenesulfonate, trifluoromethanesulfonate and the like and further reaction of the compound of general formula (X) with a compound of general formula (VI) where Ar is as defined earlier and R$^b$ is a hydroxy group.

The compound of general formula (V) may be converted to a compound of general formula (X) using halogenating agents such as thionyl chloride, CBr$_4$/PPh$_3$, CCl$_4$/PPh$_3$, phosphorus halides or by using p-toluenesulfonyl chloride, methanesulfonyl chloride, trifluoromethanesulfonyl chloride or anhydride in neat or in the presence of a base such as pyridine, DMAP, triethylamine etc. Mixture of bases may be used. These reagents may be used in 1–4 equivalents, preferably 1 to 2 equivalents. Temperature in the range –10° C. to 100° C. may be employed, preferably from 0C. to 60° C. The reaction may be conducted for 0.5 to 24 hours, preferably from 1 to 12 hours.

The reaction of compound of general formula (X) with a compound of general formula (VI) (R$^b$=OH) to produce a compound of general formula (VII) may be carried out in the presence of solvents such as THF, DMF, DMSO, DME and the like or mixture thereof The reaction may be carried out in an inert atmosphere. The inert atmosphere may be maintained by using inert gases such as N$_2$, Ar, or He. The reaction may be effected in the presence of a base such as K$_2$CO$_3$, Na$_2$CO$_3$, or NaH or their mixture. The reaction temperature may range from 20° C.–120° C., preferably at a temperature in the range of 30° C.–80° C. The duration of the reaction may range from 1–24 hours, preferably from 2 to 12 hours.

In another embodiment of this invention, the compound of general formula (VII) can also be prepared by reacting a compound of general formula (XI)

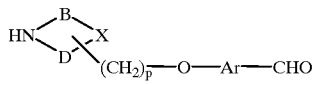

(XI)

where B, D, X, Ar and p are as defined earlier, with a compound of general formula (III).

The reaction of compound of general formula (XI) with a compound of general formula (III) may be carried out neat or in the presence of solvents such as DMF, DMSO, acetone, acetonitrile, ethanol and the like or mixture thereof. The reaction may be carried out in an inert atmosphere. The inert atmosphere may be maintained by using inert gases such as N$_2$, Ar or He. The reaction may be effected in neat or in the presence of base such as K$_2$CO$_3$, Na$_2$CO$_3$, KOH, NaOH, NaH and the like or mixture thereof. The amount of base may range from 1 to 20 equivalents, preferably 1–10 equivalents. The reaction may be carried out at a temperature in the range 20° C. to 180° C., preferably at a temperature in the range 50° C.–150° C. Duration of the reaction may range from 1 to 48 hours, preferably from 1 to 12 hours. The amounts of the compound of general formula (III) and (XI) may range from 1 to 20 equivalents, preferably from 1 to 9 equivalents.

The compound of general formula (XI) in turn can be prepared by reacting a compound of general formula (XII)

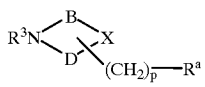

(XII)

where B, D, X, Ar and p are as defined earlier and $R^3$ is a protecting group and $R^a$ is a leaving group with a compound of general formula (VI) ($R^b$=OH) followed by removal of N-protecting group using conventional methods.

The reaction of compound of general formula (VI) ($R^b$=OH) with a compound of general formula (XII) may be carried out in the presence of solvents such as THF, DMF, DMSO, DME and the like or a mixture thereof. The reaction may be carried out in an inert atmosphere. The inert atmosphere may be maintained by using inert gases such as $N_2$, Ar, or He. The reaction may be effected in the presence of a base such as $K_2CO_3$, $Na_2CO_3$, NaH or a mixture thereof. The reaction temperature may range from 20° C. to 120° C., preferably at a temperature in the range of 30° C. to 80° C., The duration of the reaction may range from 1 to 12 hours, preferably from 2 to 6 hours. The N-protecting group $R^3$ is usually removed either by acid treatment or by hydrogenation or in the presence of a suitable base depending upon the nature of the protecting group employed.

In yet another embodiment of the present invention, the compound of the general formula (I), their tautomeric forms, their stereoisomers, their polymorphs, their pharmaceutically acceptable salts and their pharmaceutically acceptable solvates can also be prepared by reacting a compound of the general formula (V) where $R^a$ is OH group obtained and defined above with a compound of general formula (XIII).

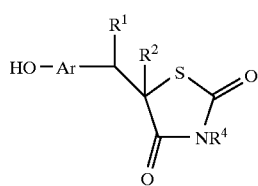

(XIII)

where $R^1$, $R^2$ and Ar are as defined earlier and $R^4$ is hydrogen or a nitrogen protecting group such as acyl or triarylmethyl group.

The reaction of compound of general formula (V) with a compound of general formula (XIII) to produce a compound of general formula (I) may be carried out using suitable coupling agents such as dicyclohexyl urea, triarylphosphine/dialkylazadicarboxylate such as $PPh_3$/DEAD, and the like. The reaction may be carried out in the presence of solvents such as THF, DME, $CH_2Cl_2$, $CHCl_3$, toluene, acetonitrile, carbontetrachloride and the like. The reaction may be carried out in an inert atmosphere. The inert atmosphere may be maintained by using inert gases such as $N_2$, Ar, or He. The reaction may be effected in the presence of DMAP-HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

In still another embodiment of the present invention, the compound of the general formula (I), their tautomeric forms, their stereoisomers, their polymorphs, their pharmaceutically acceptable salts and their pharmaceutically acceptable solvates can also be prepared by reacting a compound of the general formula (X) obtained and defined above with a compound of general formula (XIII) as defined above.

The reaction of compound of general formula (X) with a compound of general formula (XIII) to produce a compound of general formula (I) may be carried out in the presence of solvents such as THF, DMF, DMSO, DME and the like or mixture thereof. The reaction may be carried out in an inert atmosphere which is maintained by using inert gases such as $N_2$, Ar or He. The reaction may be effected in the presence of a base such as alkalis like sodium hydroxide or potassium hydroxide; alkali metal carbonates like sodium carbonate or potassium carbonate; alkali metal hydrides such as sodium hydride; organometallic bases like n-butyl lithium; alkali metal amides like sodamide, or mixture thereof. Multiple solvents and bases can be used. The amount of base may range from 1 to 5 equivalents, preferably 1 to 3 equivalents. The reaction temperature may be in the range of 0° C. to 120° C., preferably at a temperature in the range of 20° C. to 100° C. The duration of the reaction may range from 0.5 to 24 hours, preferably from 2 to 12 hours.

In still another embodiment of the present invention, the compound of general formula (I) defined above can be obtained by reacting a compound of general formula (XIV)

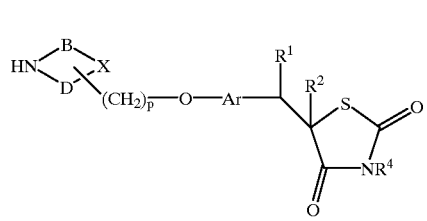

(XIV)

where B, D, $R^1$, $R^2$, $R^4$, X, Ar and p are as defined earlier, with a compound of general formula (III) defined above.

The reaction of compound of general formula (XIV) with the compound of general formula (III) to produce a compound of general formula (I) may be carried out neat or in the presence of solvents such as DMF, DMSO, acetone, acetonitrile, ethanol and THF or mixture thereof. The reaction may be carried out in an inert atmosphere. The inert atmosphere may be maintained by using inert gases such as $N_2$, Ar, or He. The reaction may be effected in the presence of base such as $K_2CO_3$, $Na_2CO_3$, KOH, NaOH, NaH and the like or a mixture thereof. The amount of base may range from 1 to 20 equivalents, preferably 1 to 6 equivalents. The reaction may be carried out at a temperature in the range 20° C. to 180° C. preferably at a temperature in the range 50° C.–150° C. Duration of the reaction may range from 1 to 48 hours, preferably from 1 to 12 hours. The amounts of the compounds of general formula (III) and (XIV) may range from 1 to 20 equivalents, preferably from 1 to 5 equivalents.

According to a feature of the invention there is provided a process for the preparation of novel intermediates of general formula (XIV) which comprises reacting a compound of general formula (XIII) with a compound of general formula (XV)

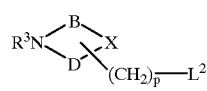

(XV)

where B, D, $R^3$, X, $L^2$, and p are as defined earlier, followed by removal of protecting group by conventional methods.

The reaction of compound of general formula (XIII) with the compound of general formula (XV) may be carried out in the presence of solvents such as THF, DMF, DMSO, DME and the like or a mixture thereof. The reaction may be carried out in an inert atmosphere. The inert atmosphere may be maintained by using inert gases such as N₂, Ar, or He. The reaction may be effected in the presence of a base such as K₂CO₃, Na₂CO₃, NaH or their mixture. The reaction temperature may range from 20° C. to 120° C., preferably at a temperature in the range of 30° C. to 80° C. The duration of the reaction may range from 1 to 12 hours, preferably from 2 to 6 hours.

According to another embodiment of the present invention, the compound of the general formula (XIV), where R¹ and R² together represent a bond can also be prepared by reacting a compound of general formula (XVI)

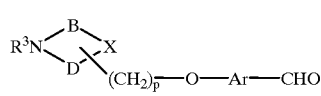
(XVI)

where B, D, Ar, X and p are defined as earlier and R³ is a protecting group excluding A—(CH₂)ₖ—O—C(=Y)— where A represents aryl or heteroaryl group, k is an integer ranging between 1–4 and Y is a heteroatom selected from O, S or NR where R may be H or lower alkyl or alkoxy group, with 2,4-thiazolidinedione; followed by removal of N-protecting group by conventional methods.

The reaction between the compound of general formula (XVI) with 2,4-thiazolidinedione may be carried out neat in the presence of sodium acetate or in the presence of a solvent such as benzene, toluene, or methoxyethanol. Mixture of solvents may be used. The reaction temperature may range from 80° C. to 140° C. depending upon the solvents employed. A suitable catalyst such as piperidinium acetate or benzoate or sodium acetate may also be employed. The water produced in the reaction may be removed, for example, by using Dean Stark water separator or by using water absorbing agents like molecular sieves.

In another embodiment of the present invention, the compound of general formula (I) where A, B, D, X, p and Ar are as defined earlier can be prepared by the reaction of compound of general formula (XVII)

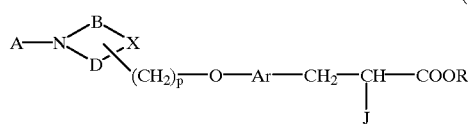
(XVII)

where A, B, D, X, p and Ar are as defined earlier, J is a halogen atom like chlorine, bromine or iodine and R is a lower alkyl group, with thiourea followed by treatment with an acid.

The reaction of compound of general formula (XVII) with thiourea is normally carried out in the presence of alcoholic solvent such as methanol, ethanol, propanol, isobutanol, 2-methoxybutanol etc. or DMSO or sulfolane. The reaction may be conducted at a temperature in the range between 20° C. and the reflux temperature of the solvent used. Bases such as NaOAc, KOAc, NaOMe, NaOEt etc. can be used. The reaction is normally followed by treatment with a mineral acid such as hydrochloric acid at 20° C.–100° C.

The compound of general formula (XVII) where J is a halogen atom can be prepared by the diazotization of the amino compound of the general formula (XVIII)

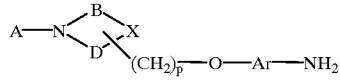
(XVIII)

where all symbols are as defined earlier, using alkali metal nitrites followed by treatment with acrylic acid esters in the presence of hydrohalo acids and catalytic amount of copper oxide or copper halide.

The compound of general formula (XVIII) can in turn be prepared by the conventional reduction of the novel intermediate (XIX) where all symbols are as defined earlier.

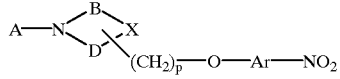
(XIX)

The novel intermediate of general formula (XIX) can be prepared by the reaction of compound of general formula (V)

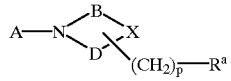
(V)

where A, B, D, X and p are as defined earlier and Rᵃ is a hydroxy group or a leaving group with a compound of general formula (XX)

$$R^b—Ar—NO_2 \qquad (XX)$$

where Rᵇ is a halogen atom such as chlorine or fluorine or a hydroxy group and Ar is as defined earlier.

The reaction of compound of formula (V) with a compound of formula (XX) to produce a compound of the formula (XIX) may be carried out in the presence of solvents such as THF, DMF, DMSO, DME and the like or mixtures thereof. The reaction may be carried out in an inert atmosphere which is maintained by using inert gases such as N₂, Ar, or He. The reaction may be effected in the presence of a base such as K₂CO₃, Na₂CO₃ or NaH or mixtures thereof. The reaction temperature may range from 20° C.–120° C., preferably at a temperature in the range of 30° C.–100° C. The duration of the reaction may range from 1–12 hours, preferably from 2 to 6 hours.

In another embodiment of this invention, the compound of general formula (XIX) can also be prepared by reacting a compound of general formula (XXI)

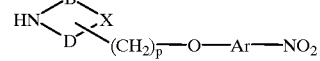
(XXI)

where B, D, X, Ar and p are as defined earlier, with a compound of general formula (III).

The reaction of compound of general formula (XXI) with a compound of general formula (III) may be carried out neat or in the presence of solvents such as DMF, DMSO, acetone, acetonitrile or ethanol. Mixture of solvents may be used. The inert atmosphere may be maintained by using inert gases such as N₂, Ar or He. The reaction may be effected in neat or in the presence of base such as $K_2CO_3$, $Na_2CO_3$, KOH, NaOH, NaH and the like or mixture thereof. The amount of base may range from 1 to 20 equivalents, preferably 1–10 equivalents. The reaction may be carried out at a temperature in the range of 20° C. to 180° C., preferably at a temperature in the range of 50° C.–150° C. Duration of the reaction may range from 1 to 48 hours, preferably from 1 to 12 hours. The amounts of the compound of general formula (III) and (XXI) may range from 1 to 20 equivalents, preferably from 1 to 9 equivalents.

The compound of general formula (XXI) in turn can be prepared by reacting a compound of general formula (XII)

(XII)

where B, D, X, Ar and p are as defined earlier and $R^3$ is a protecting group and $R^a$ is a leaving group with a compound of general formula (XX) ($R^b$=OH) followed by removal of N-protecting group using conventional methods.

The reaction of compound of general formula (XX) ($R^b$=OH) with a compound of general formula (XII) may be carried out in the presence of solvents such as THF, DMF, DMSO, DME and the like. Mixture of solvents may be used. An inert atmosphere may be used and the inert atmosphere may be maintained by using inert gases such as $N_2$, Ar, or He. The reaction may be effected in the presence of a base such as $K_2CO_3$, $Na_2CO_3$, or NaH. The reaction temperature may range from 20° C. to 120° C., preferably at a temperature in the range of 30° C. to 80° C. The duration of the reaction may range from 1 to 12 hours, preferably from 2 to 6 hours. The N-protecting group $R^3$ is usually removed either by acid treatment or by hydrogenation or in the presence of a suitable base depending upon the nature of the protecting group employed.

Conventional deprotection methods include treatment with acid such as, hydrochloric acid, trifluoroacetic acid or bases such as, KOH, NaOH, $Na_2CO_3$, $NaHCO_3$, or $K_2CO_3$ and the like. These reagents may be used as aqueous solution or as solutions in alcohols like methanol, ethanol etc. Deprotection can also be effected by gaseous hydrogen in the presence of catalyst such as Pd/carbon or conventional transfer hydrogenation methods, when the protecting group is a benzyl or a substituted benzyl group.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guanidine and their derivatives etc. may also be used. Alternatively, acid addition salts are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzene sulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like or chiral bases such as brucine, cinchona alkaloids and their derivatives and the like.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray data or such other techniques.

The present invention also provides a pharmaceutical composition, containing the compounds of the general formula (I), as defined above, their tautomeric forms, their stereoisomers, their polymorphs, their pharmaceutically acceptable salts, their pharmaceutically acceptable solvates in combination with the usual pharmaceutically employed carriers, diluents and the like, useful for the treatment and/or prophylaxis of diseases in which insulin resistance is the underlying pathophysiological mechanism such as type II diabetes, impaired glucose tolerance, dyslipidaemia, hypertension, coronary heart disease and other cardiovascular disorders including atherosclerosis; insulin resistance associated with obesity and psoriasis, for treating diabetic complications and other diseases such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 25%, preferably 1 to 15% by weight of active compound, the remainder of the composition being pharmaceutically acceptable carriers, diluents or solvents.

A typical tablet production method is exemplified below:

Tablet Production Example:

| Tablet Production Example: | | |
|---|---|---|
| a) 1) Active ingredient | 30 | g |
| 2) Lactose | 95 | g |
| 3) Corn starch | 30 | g |
| 4) Carboxymethyl cellulose | 44 | g |
| 5) Magnesium stearate | 1 | g |
| | 200 | g for 1000 tablets |

The ingredients 1 to 3 are uniformly blended with water and granulated after drying under reduced pressure. The ingredients 4 and 5 are mixed well with the granules and compressed by a tabletting machine to prepare 1000 tablets each containing 30 mg of active ingredient.

| b) | 1) Active ingredient | 30 g |
|---|---|---|
|  | 2) Calcium phosphate | 90 g |
|  | 3) Lactose | 40 g |
|  | 4) Corn starch | 35 g |
|  | 5) Polyvinyl pyrrolidone | 3.5 g |
|  | 6) Magnesium stearate | 1.5 g |
|  |  | 200 g for 1000 tablets |

The ingredients 1 to 4 are uniformly moistened with an aqueous solution of ingredient 5 and granulated after drying under reduced pressure. Ingredient 6 is added and granules are compressed by a tabletting machine to prepare 1000 tablets containing 30 mg of active ingredient 1.

The compound of the formula (I) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 200 mg/kg body weight of the subject per day or preferably about 0.10 to about 50 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in the amounts sufficient to provide the desired dosage in the range as described above Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly, with intramuscular administration being preferred in humans.

The invention is explained in detail in the examples given below which are provided by way of illustration only and therefore should not be construed to limit the scope of the invention.

Preparation 1

(S)-2-Hydroxymethyl-1-(pyridin-2-yl) pyrrolidine:

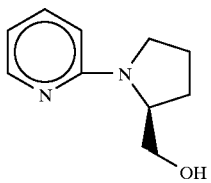

A mixture of 2-chloropyridine (118 g) and L-prolinol (70 g) was heated under nitrogen atmosphere at 160° C. with stirring for 4 h. The mixture was cooled to room temperature and poured into water and the solution was extracted with chloroform repeatedly. The combined organic extracts were dried ($Na_2SO_4$) and concentrated. The crude product was purified by column chromatography using 2% MeOH in $CHCl_3$ as eluent to get 67.3 g (54.5%) of the title compound as a syrupy liquid.

$^1$H NMR ($CDCl_3$, 200 MHz): d 1.7 (m, 1H), 2.05 (m, 3H), 3.2–3.9 (m, 4H), 4.25 (m, 1H), 6.43 (d, J=8.4 Hz, 1H), 6.58 (t, J=6.0 Hz, 1H), 7.5 (m, 1H), 8.02 (d, J=4.2 Hz, 1H).

Preparation 2

1-(Pyridin-2-yl)-4-piperidinol:

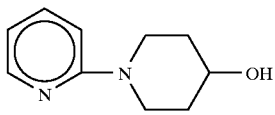

The title compound (3.5 g, 50%) was prepared as a semi solid from 2-chloropyridine (6.7 g) and 4-piperidinol (4 g) by an analogous procedure to that described in preparation 1.

$^1$H NMR ($CDCl_3$, 200 MHz): d 1.6 (m, 2H), 2.0 (m, 2H), 3.15 (m, 2H), 3.9 (m, 1H), 4.1 (m, 2H), 6.59 (m, 1H), 6.67 (d, J=8.6 Hz, 1H), 7.45 (m, 1H), 8.17 (d, J =3.6 Hz, 1H).

Preparation 3

4-Hydroxymethyl-1-(pyridin-2-yl) piperidine:

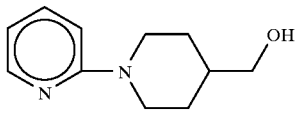

The title compound (2.7 g, 80%) was prepared as a syrupy liquid from 2-chloropyridine (7.8 g) and 4-hydroxymethylpiperidine (2 g) by an analogous procedure to that described in preparation 1.

$^1$H NMR ($CDCl_3$, 200 MHz): d 1.3 (m, 2H), 1.8 (m, 3H), 2.84 (t, J=11.7 Hz, 2H), 3.54 (d, J=6.2 Hz, 2H), 4.32 (approx. d, J=13.0 Hz, 2H), 6.59 (t, J=5.9 Hz, 1H), 6.67 (d, J=8.8 Hz, 1H), 7.46 (m, 1H), 8.18 (d, J=3.6 Hz, 1H).

Preparation 4
1-(Pyridin-2-yl)piperidin-4-yl methanesulfonate:

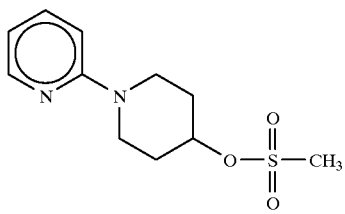

To an ice cooled solution of the product obtained in preparation 2 (3.25 g) and triethylamine (8 ml) in dichloromethane (30 ml) at ca 0° C. was added methanesulphonyl chloride (1.7 ml). The mixture was stirred for 12 h at room temperature. At the end of this time, the reaction mixture was washed with water, dried (CaCl$_2$) and concentrated to get 4.7 g (100%) of the title compound. mp 66–68° C.

$^1$H NMR (CDCl$_3$, 200 MHz): d 1.8–2.2 (m, 4H), 3.06 (s, 3H), 3.4 (m, 2H), 3.9 (m, 2H), 5.0 (m, 1H), 6.7 (m, 2H), 7.5 (m, 1H), 8.18 (d, J=3.6 Hz, 1H).

Preparation 5
[1-(Pyridin-2-yl)piperidin-4-yl]methyl methanesulfonate:

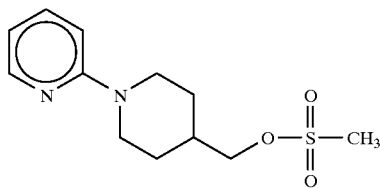

The title compound (2.1 g, 83%) was prepared as a semi solid from 4-hydroxymethyl-1-(pyridin-2-yl)piperidine (1.8 g), obtained in preparation 3 and methanesulphonyl chloride (0.8 ml) by a similar procedure to that used in preparation 4.

$^1$H NMR (CDCl$_3$, 200 MHz): d 1.35 (m, 2H), 1.8–2.15 (m, 3H), 2.85 (t, J=12.2 Hz, 2H), 3.02 (s, 3H), 4.1 (d, J=6.2 Hz, 2H), 4.35 (approx. d, J=12.8 Hz, 2H), 6.6 (m, 2H), 2.48 (t, J=7.8 Hz, 1H), 8.18 (d, J=3.8 Hz, 1H).

Preparation 6
4-[1-(Ethoxycarbonyl)piperidin-4-yloxy]benzaldehyde:

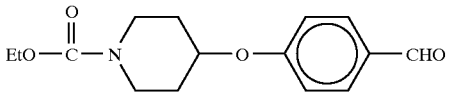

To a mixture of 1-(ethoxycarbonyl)piperidin-4-yl methanesulfonate (10 g) and 4-hydroxy benzaldehyde (5.8 g) in dry DMF (75 ml), K$_2$CO$_3$ (11 g) was added and the mixture was stirred at 80° C. for 12 h. At the end of this time, the reaction mixture was cooled, added water and extracted with EtOAc. The EtOAc extract was washed with 5% aqueous Na$_2$CO$_3$ solution followed by brine and dried over anhydrous sodium sulphate. The solvent was then removed by distillation under reduced pressure to give 7 g (63.6%) of the title compound as a semi solid.

$^1$H NMR (CDCl$_3$, 200 MHz): d 1.28 (t, J=7 Hz, 3H), 1.7–2.1 (m, 4H), 3.45 (m, 2H), 3.75 (m, 2H), 4.15 (q, J=7 Hz, 2H), 4.63 (m, 1H), 7.01 (d, J=8.6 Hz, 2H), 7.84 (d, J=8.8 Hz, 2H), 9.89 (s, 1H).

Preparation 7
4-(Piperidin-4-yloxy)benzaldehyde:

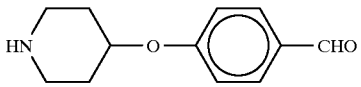

A mixture of the compound obtained in preparation 6 (4.5 g) and conc. HCl (40 ml) was stirred at 100° C. for 12 h. The reaction mixture was concentrated in vacuo. The residue was diluted with water, neutralized with saturated aqueous NaHCO$_3$ solution and extracted with CHCl$_3$, dried (CaCl$_2$) and concentrated in vacuo to get 3 g (90%) of the title compound as a semi solid.

$^1$H NMR (CDCl$_3$, 200 MHz): d 1.75 (m, 2H), 2.05 (m, 2H), 2.75 (m, 2H), 3.2 (m, 2H), 4.55 (m, 1H), 7.01 (d, J=8.6 Hz, 2H), 7.83 (d, J=8.6 Hz, 2H) 9.89 (s, 1H).

Preparation 8
(S)-4-[[1-(Pyridin-2-yl)pyrrolidin-2-yl]methoxy]benzaldehyde:

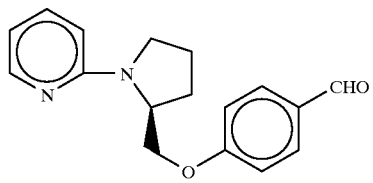

A solution of 40 g of the product obtained in preparation 1 in 300 ml of DMF was added dropwise while cooling to a suspension of 16.1 g of (60% w/w dispersion) sodium hydride in 300 ml of DMF. The mixture was then stirred for 1 h at room temperature, after which 47.7 ml of 4-fluorobenzaldehyde in 200 ml of DMF was added dropwise at room temperature. The reaction mixture was then stirred at 80° C. for 4 h. At the end of this time, water was added to the reaction mixture. The mixture was extracted with EtOAc and dried over anhydrous sodium sulphate. The solvent was evaporated to dryness under reduced pressure. The crude product was chromatographed on silica gel using 5–10% (gradient elution) of EtOAc in petroleum ether to afford 42.5 g (67%) of the title compound as a semi solid.

$^1$H NMR (CDCl$_3$, 200 MHz): d 2.1 (m, 4H), 3.3 (m, 1H), 3.5 (m, 1H), 3.96 (t, J=8.7 Hz, 1H), 4.4 (dd, J=9.6 and 3.4 Hz, 1H), 4.55 (m, 1H), 6.41 (d, J=8.8 Hz, 1H), 6.59 (m, 1H), 7.13 (d, J=8.8 Hz, 2H), 7.46 (m, 1H), 7.82 (d, J=8.8 Hz, 2H), 8.18 (d, J=3.8 Hz, 1H), 9.87 (s, 1 H).

Preparation 9
4-[1-(Pyridin-2-yl)piperidin-4-yloxy]benzaldehyde:

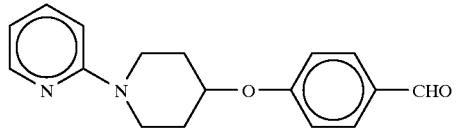

Method A:

To a mixture of t-(pyridin-2-yl)piperidin-4-yl methanesulfonate (4.5 g) obtained in preparation 4 and 4-hydroxybenzaldehyde (2.5 g) in dry DMF (30 ml), K$_2$CO$_3$ (9.7 g) was added and the mixture was stirred at 80° C. for 10 h. At the end of this time, the reaction mixture was cooled, water added and extracted with EtOAc. The EtOAc extract was washed with 5% aqueous Na₂CO₃ solution followed by brine and dried over anhydrous sodium sulphate. The solvent was then removed by distillation under reduced pressure to give 1.8 g (36.3%) of the title compound. mp 114–116° C.

Method B:

The title compound (0.6 g, 43%) was also prepared as a pale yellow solid (mp: 114–116° C.) from 4-(4-piperidinyloxy)benzaldehyde (1.0 g), obtained in preparation 7 and 2-chloropyridine (3.6 ml) by an analogous procedure to that described in preparation 1.

¹H NMR (CDCl₃, 200 MHz) : d 1.9 (m, 2H), 2.1 (m, 2H), 3.5 (m, 2H), 3.9 (m, 2H), 4.7 (m, 1 H), 6.7 (m, 2), 7.03 (d, J=8.6 Hz, 2H), 7.49 (m, 1H), 7.85 (d, J=8.8 Hz, 2H), 8.2 (d, J=3.4 Hz, 1H), 9.89 (s, 1H).

Preparation 10

4-[[1-(Pyridin-2-yl)piperidin-4-yl]methoxy]benzaldehyde:

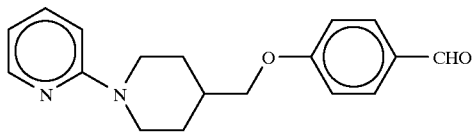

The title compound (1.0 g, 45%) was prepared as a semi solid from [1-(pyridin-2-yl)piperidin-4-yl]methyl methanesulfonate (2.0 g) obtained in preparation 5 and 4-hydroxybenzaldehyde (1.1 g) by an analogous procedure to that described in method A of preparation 9.

¹H NMR (CDCl₃, 200 MHz): d 1.45 (m, 2H), 1.8–2.25 (m, 3H), 2.89 (m, 2H), 3.92 (d, J=6.2 Hz, 2H), 4.36 (approx. d, J=12.8 Hz, 2H), 6.62 (m, 2H), 6.99 (d, J=8.6 Hz, 2H), 7.47 (m, 1H), 7.83 (d, J=8.6 Hz, 2H), 8.19 (d, J=3.6 Hz, 1H), 9.88 (s, 1H).

Preparation 11

4-[2-[4-(Pyridin-2-yl)piperazin-1-yl]ethoxy]benzaldehyde:

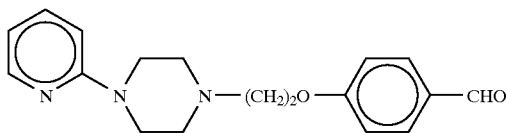

The title compound (2.0 g, 84%) was prepared as a thick liquid from 2-[4-(pyridin-2-yl) piperazin-1-yl]ethyl chloride, HCl salt (2 g) and 4-hydroxybenzaldehyde (1.4 g) in a similar manner to that described in Method A of preparation 9.

¹H NMR (CDCl₃, 200 MHz): d 2.78 (t, J 4.6 Hz, 4H), 2.96 (t, J=5.6 Hz, 2H), 3.64 (t, J=5 Hz, 4H), 4.29 (t, J=5.4 Hz, 2H), 6.66 (m, 2H), 7.03 (d, J=8.6 Hz, 2H), 7.5 (m, 1H), 7.85 (d, J=8.6 Hz, 2H), 8.2 (d, J=3.8 Hz, 1H), 9.9 (s, 1H).

Preparation 12

(S)-2-Hydroxymethyl-1-(quinolin-2-yl)pyrrolidine:

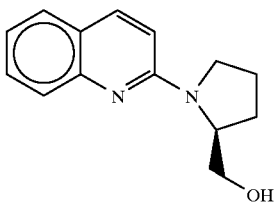

The title compound (6 g, 100%) was prepared as a syrupy liquid from 2-chloroquinoline (4 g) and L-prolinol (14.8 g) by an analogous procedure to that described in preparation 1.

¹H NMR (CDCl₃, 200 MHz): d 1.7 (m, 1H), 2.1 (m, 3H), 3.4–3.9 (m, 4H), 4.5 (m, 1H), 6.76 (d, J=9.0 Hz, 1H), 7.2 (m, 1H), 7.6 (m, 3H), 7.89 (d, J=9.0 Hz, 1H).

Preparation 13

(S)-4-[[1-(Quinolin-2-yl)pyrrolidin-2-yl]methoxy]benzaldehyde:

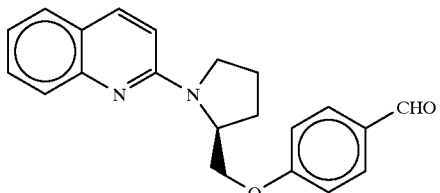

The title compound (1.6 g, 37%) was prepared as a thick liquid from (S)-2-hydroxymethyl-1-(quinolin-2-yl) pyrrolidine (3 g) obtained in preparation 12 and 4-fluorobenzaldehyde (2.8 ml) in a similar manner to that described in preparation 8.

¹H NMR (CDCl₃, 200 MHz) : d 2.2 (m, 4H), 3.45 (m, 1H), 3.7 (m, 1H), 4.0 (t, J=9.3 Hz, 1H), 4.64 (dd, J=10.0 and 3.0 Hz, 1H), 4.8 (m, 1H), 6.8 (d, J=9.0 Hz, 1H), 6.9–8.0 (complex, 9H), 9.9 (s, 1H).

Preparation 14

(S)-4-[[1-(Quinolin-2-yl)pyrrolidin-2-yl]methoxy]nitrobenzene:

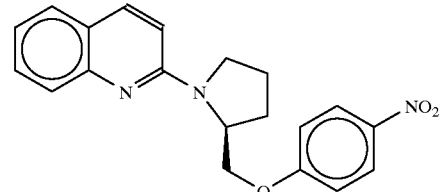

A solution of 16.5 g of the product obtained in preparation 12 in DMF (100 ml) was added dropwise to a suspension of 5.2 g (50% w/w dispersion in mineral oil) of sodium hydride in DMF (50 ml). The mixture was stirred at room temperature for 0.5 h, after which 12.3 g of 1-fluoro-4-nitrobenzene was added dropwise and the mixture was then stirred at the same temperature for 12 h. At the end of this time, water was added, the resulting solid was filtered, washed with excess of water and dried to afford 9 g (36%) of the title compound. mp 118–120° C.

¹H NMR (CDCl₃, 200 MHz): d 2.15 (m, 4H), 3.45 (m, 1H), 3.7 (m, 1H), 4.0 (t, J=9.4 Hz, 1H), 4.65 (dd, J=10.0 and 3.2 Hz, 1H), 4.8 (bs, 1H), 6.77 (d, J=9.2 Hz, 1H), 7.25 (m, 1H), 7.38 (d, J=9.2 Hz, 2H), 7.65 (m, 2H), 7.75 (d, J=8.4 Hz, 1H), 7.91 (d, J=9.0 Hz, 1H), 8.25 (d, J=9.2 Hz, 2H).

Preparation 15

(S)-4-[[1-(Quinolin-2-yl)pyrrolidin-2-yl]methoxy] aniline:

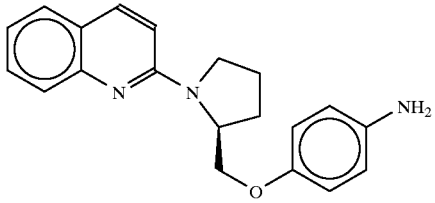

To a solution of (S)-4-[[1-(quinolin-2-yl)pyrrolidin-2-yl]methoxy]nitrobenzene (6 g) obtained in preparation 14 in EtOH (40 ml) and conc. HCl (40 ml), iron powder (9.6 g) was added in small portions. The reaction mixture was stirred at room temperature for 1 h. The solution was filtered and the filtrate was evaporated to dryness. The residue was diluted with $H_2O$ and neutralized (pH: 7 ) with aqueous $NaHCO_3$ solution and extracted with $CHCl_3$, dried ($CaCl_2$) and concentrated to get 5.5 g (100%) of the title compound as a dark colored solid. mp. 138–140° C.

$^1$H NMR ($CDCl_3$, 200 MHz): d 2.15 (m, 4H), 3.5 (m, 1H), 3.6–4.0 (m, 2H), 4.37 (dd, J=10.0 and 3.4 Hz, 1H), 4.7 (bs, 1H), 6.68 (d, J=8.8 Hz, 2H), 6.79 (d, J=9.2 Hz, 1H), 6.98 (d, J=8.8 Hz, 2H), 7.72 (t, J=7.6 Hz, 1H), 7.6 (m, 2H), 7.74 (d, J=8.2 Hz, 1H), 7.87 (d, J=9.0 Hz, 1H).

Preparation 16

Ethyl 2-bromo-3-[4-[[1-(quinolin-2-yl)-(2S)-pyrrolidin-2-yl]methoxy]phenyl]propanoate:

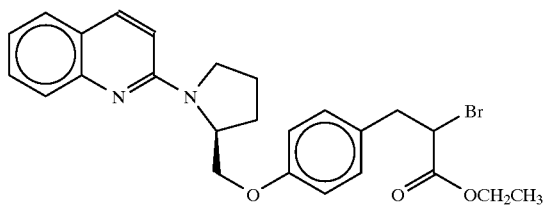

A solution of $NaNO_2$ (1.2 g) in water (2.1 ml) was added dropwise to a stirred ice cooled mixture of (S)-4-[[1-(quinolin-2-yl)pyrrolidin-2-yl]methoxy]aniline (5 g) obtained in preparation 15, aqueous HBr (48%, 8.5 ml), MeOH (15 ml) and acetone (37 ml) below 5C. The solution was stirred at 5° C. for 30 min and ethyl acrylate (10 ml) was added and the temperature was raised to 60° C. Powder $Cu_2O$ (140 mg) was added in small portions to the vigorously stirred mixture. After the $N_2$ gas evolution has ceased the reaction mixture was concentrated in vacuo. The residue was diluted with water, made alkaline with concentrated $NH_4OH$ and extracted with EtOAc. The EtOAc extract was washed with brine, dried ($Na_2SO_4$) and concentrated in vacuo. The crude product was chromatographed on silica gel using 0–10% (gradient elution) of methanol in chloroform to afford 2.6 g (34%) of the title compound as a thick liquid.

$^1$H NMR ($CDCl_3$, 200 MHz): d 1.25 (t, J=7.2 Hz, 3H), 2.15 (m, 4H), 3.2 (dd, J=14.0 and 6.8 Hz, 1H), 3.35–3.6 (m, 2H), 3.7 (m, 1H), 3.89 (t, J=9.4 Hz, 1H), 4.2 (m, 2H), 4.3–4.6 (m, 2H), 4.8 (bs, 1H), 6.79 (d, J=9 Hz, 1H), 7.2 (m, 5H), 7.6 (m, 2H), 7.75 (d, J=8.2 Hz, 1H), 7.88 (d, J=9.0 Hz, 1H).

Preparation 17

(S)-2-Hydroxymethyl-1-(lepidin-2-yl)pyrrolidine:

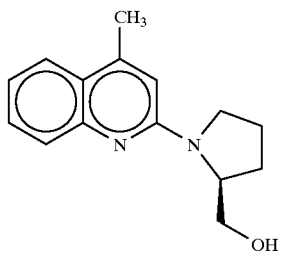

The title compound (22 g, 94%) was prepared as thick liquid from 2-chlorolepidine (17.3 g) and L-prolinol (59 g) by an analogous procedure to that described in preparation 1.

$^1$H NMR ($CDCl_3$, 200 MHz): d 1.7 (m, 1H), 2.1 (m, 3H), 2.6 (s, 3H), 3.4–3.9 (m, 4H), 4.5 (m, 1H), 6.6 (s, 1H), 7.25 (m, 1H), 7.52 (t, J=7.4 Hz, 1H), 7.62 (d, J=8.0 Hz, 1H), 7.75 (d, J 8.0 Hz, 1H).

Preparation 18

(S)-4-[[1-(lepidin-2-yl)pyrrolidin-2-yl]methoxy] benzaldehyde:

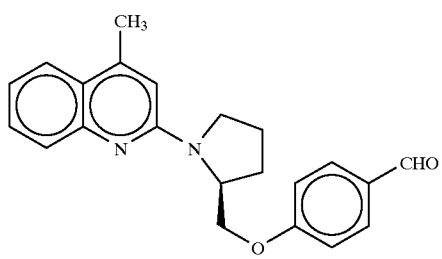

The title compound (0.25, 35%) was prepared as a thick liquid from (S)-2-Hydroxymethyl-1-(lepidin-2-yl) pyrrolidine (0.5 g), obtained in preparation 17 and 4-fluorobenzaldehyde (0.33 ml) in a similar manner to that described in preparation 8.

$^1$H NMR ($CDCl_3$, 200 MHz): d 2.15 (m, 4H), 2.6 (s, 3H), 3.45 (m, 1H), 3.7 (m, 1H), 4.0 (t, J=9. 4 Hz, 1H), 4.65 (m, 1H), 4.8 (m, 1H), 6.65 (s, 1H), 7.2–8.05 (complex, 8 H), 9.9 (s, 1H).

Preparation 19

(S)-4-[[1-(Lepidin-2-yl)pyrrolidin-2-yl]methoxy nitrobenzene:

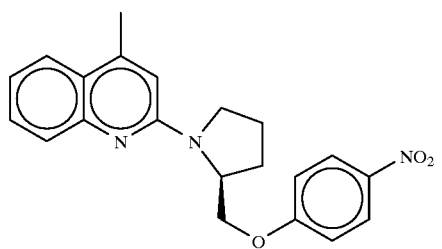

The title compound (8 g, 53%) was prepared as an yellow solid (S)-2-hydroxymethyl-1-(lepidin-2-yl)pyrrolidine (10 g), obtained in preparation 17 and 1-fluoro-4-nitrobenzene (5.3 ml) by a similar procedure to that used in preparation 14.

$^1$H NMR ($CDCl_3$, 200 MHz): d 2.15 (m, 4H), 2.6 (s, 3H), 3.4 (m, 1H), 3.65 (m, 1H), 4.0 (t, J=9.5 Hz, 1H), 4.65 (dd,

J=10 and 3 Hz, 1H), 4.8 (bs, 1H), 6.65 (s, 1H), 7.25 (t, J=7.4 Hz, 1H), 7.37 (d, J=9.2 Hz, 2H), 7.1 (m, 1H), 7.7 (t, J=8.6 Hz, 2H), 8.24 (d, J=9.2 Hz, 2H).

Preparation 20

(S)-4-[[1-(lepidin-2-yl)pyrrolidin-2-yl]methoxy]aniline:

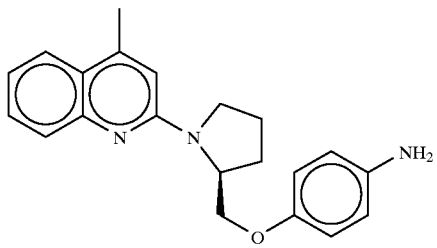

(S)-4-[[1-(Lepidin-2-yl)pyrrolidin-2-yl]methoxy nitrobenzene (5 g), obtained in preparation 19 was dissolved in EtOAc (20 ml) and was reduced with hydrogen (50 psi) in the presence of 10% palladium on charcoal (0.5 g) at ambient temperature until hydrogen uptake (nearly 16 h) ceased. The solution was filtered through a bed of celite, the filter pad was washed exhaustively with EtOAc. The combined filtrate was evaporated to dryness under reduced pressure. The crude product was chromatographed on silica gel using 1 to 10% (gradient elution) of methanol in chloroform to afford 4.6 g (100%) of the title compound as a thick liquid.

$^1$H NMR (CDCl$_3$, 200 MHz): d 2.1 (m, 4H), 2.6 (s, 3H), 3.5 (m, 1H), 3.6–3.9 (m, 2H), 4.35 (dd, J=9.8 and 3.2 Hz, 1H), 4.7 (bs, 1H), 6.7 (m, 3H), 7.0 (d, J=8.6 Hz, 2H), 7.24 (m, 1H), 7.5 (m, 1H), 7.76 (t, J=7.2 Hz, 2H).

Preparation 21

Ethyl 2-chloro-3-[4-[[1-(lepidin-2-yl)-(2S)-pyrrolidin-2-yl] methoxy]phenyl]propanoate:

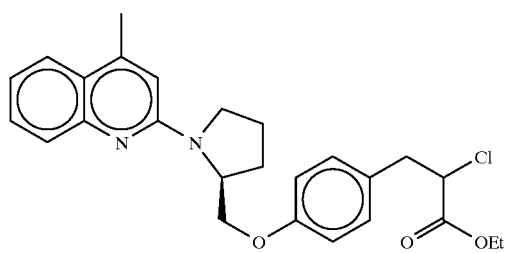

The title compound (15 g, 85%) was prepared as a thick liquid from (S)-4-[[1-(lepidin-2-yl)pyrrolidin-2-yl] methoxy]aniline (13.7 g), obtained in preparation 20, by a similar procedure to that described in preparation 16 except HCl was used instead of HBr.

$^1$H NMR (CDCl$_3$, 200 MHz): d 1.25 (t, J=7.2 Hz, 3H), 2.15 (m, 4H), 2.6 (s, 3H), 3.12 (dd, J=14.0 and 7.6 Hz, 1H), 3.32 (dd, J=14.2 and 7.6 Hz, 1H), 3.5 (m, 1H), 3.7 (m, 1H), 3.86 (t, J=9.2 Hz, 1H), 4.2 (q, J=7.2 Hz, 2H), 4.4 (m, 2H), 4.7 (bs, 1H), 6.65 (s, 1H), 7.2 (m, 5H), 7.6 (m, 1H), 7.77 (t, J=6.8 Hz, 2H).

Preparation 22

Ethyl 2-bromo-3-[4-[[1-(lepidine-2-yl)-(2S)-pyrrolidin-2-yl] methoxy]phenyl]propanoate:

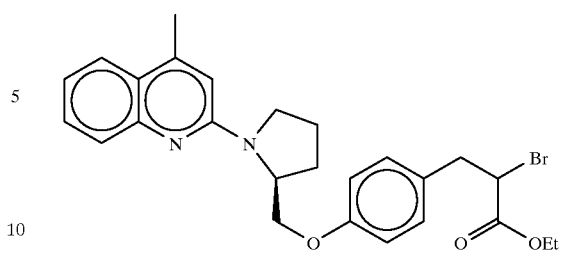

The title compound (1.5 g, 23%) was prepared as a thick liquid from (S)-4-[[1-(lepidine-2-yl)pyrrolidin-2-yl] methoxy]aniline (4.6 g), obtained in preparation 20, by a similar procedure to that described in preparation 16.

$^1$H NMR (CDCl$_3$, 200 MHz): d 1.26 (t, J=7.2 Hz, 3H), 2.15 (m, 4H), 2.6 (s, 3H), 3.21 (dd, J=14.2 and 7.0 Hz, 1H), 3.35–3.6 (m, 2H), 3.7 (m, 1H), 3.9 (m, 1H), 4.2 (m, 2H), 4.37 (t, J=7.8 Hz, 1H), 4.48 (dd, J=9.8 and 3.4 Hz, 1H), 4.75 (bs, 1H), 6.7 (s, 1H), 7.1–7.4 (m, 5H), 7.6 (m, 1H), 7.8 (m, 2H).

Preparation 23

(3R)-Hydroxy-1-(pyridin-2-yl)pyrrolidine:

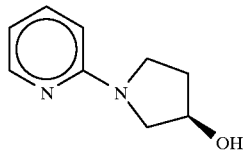

The title compound (2.9 g, 15%) was prepared as a thick liquid from 2-chloropyridine (40 g) and L-prolinol (10 g) by an analogous procedure to that described in preparation 1.

$^1$H NMR (CDCl$_3$, 200 MHz): d 2.1 (m, 2H), 2.8 (bs, exchangeable with D$_2$O, 1H), 3.6 (m, 4H), 4.6 (bs, 1H), 6.35 (d, J=8.4 Hz, 1H), 6.55 (m, 1H), 7.45 (m, 1H), 8.13 (d, J=4.6 Hz, 1H).

Preparation 24

(3R)-1-pyridin-2-yl)-3-pyrrolidine methane sulfonate:

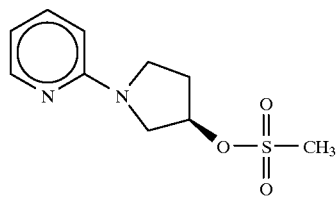

The title compound (0.3 g, 100%) was prepared as a thick liquid from (3R)-3-hydroxy-1-(pyridin-2-yl)pyrrolidine (0.2 g), obtained in preparation 23 and methanesulfonyl chloride (0.18 ml) by a similar procedure to that used in preparation 4.

$^1$H NMR (CDCl$_3$, 200 MHz): d 2.35 (m, 2H), 3.0 (s, 3H), 3.65 (m, 2H), 3.8 (m, 2H), 5.4 (m, 1H), 6.38 (d, J=8.4 Hz, 1H), 6.6 (m, 1H), 7.5 (m, 1H), 8.16 (d, J=4.0 Hz, 1H).

Preparation 25

(3S)-4-[1-(Pyridin-2-yl)pyrrolidin-3-yloxy]benzaldehyde:

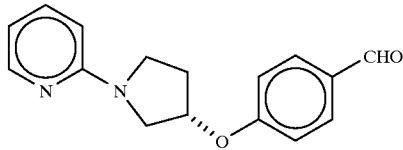

The title compound (0.15 g, 68%) was prepared as a thick liquid from (3R)-1-(pyridin-2-yl)-3-pyrrolidine methane sulfonate (0.2 g), obtained in preparation 24 and 4-hydroxybenzaldehyde (0.12 g) by an analogous procedure to that described in method A of preparation 9.

$^1$H NMR (CDCl$_3$, 200 MHz): d 2.35 (m, 2H), 3.65 (m, 2H), 3.8 (m,2H), 5.15 (bs, 1H), 6.4 (m, 1H), 6.6 (m, 1H), 7.0 (d, J=8.8 Hz, 2H), 7.45 (m, 1H), 7.84 (d, J=8.6 Hz, 2H), 8.16 (d, J=2.8 Hz, 1H), 9.89 (s, 1H).

Preparation 26

2-Hydroxymethyl-4-(pyridin-2-yl)morpholine:

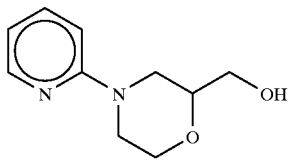

The title compound (33.0 g, 72%) was prepared as a thick liquid from 2-chloropyridine (54.32 g) and 2-hydroxymethyl morpholine (28.0 g) by a similar procedure to that described in preparation 1.

$^1$H NMR (CDCl$_3$, 200 MHz): d 2.70–2.90 (m, 1H), 2.98 (td, J=11.95 and 3.33 Hz, 1H), 3.56–3.90 (m, 4H), 3.90–4.20 (m, 3H), 6.58–6.79 (m, 2H), 7.51 (t, J=6.89 Hz, 1H), 8.20 (d, J=3.73 Hz, 1H).

Preparation 27

4-[[4-(Pyridin-2-yl)morpholin-2-yl]methoxy]benzaldehyde:

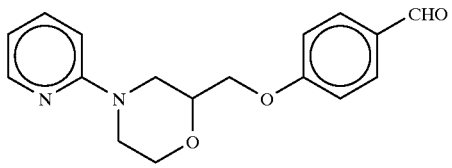

The title compound (39.0 g, 76%) was prepared as a syrupy liquid from 2-hydroxymethyl-4-(pyridin-2-yl) morpholine (33.5 g) obtained from preparation 26 and 4-fluorobenzaldehyde (27.85 g) by a similar procedure to that described in preparation 8.

$^1$H NMR (CDCl$_3$, 200 MHz): d 2.89 (td, J=12.36 and 1.89 Hz, 1H), 3.05 (td, J=12.36 and 3.46 Hz, 1H), 3.70–4.40 (m, 7H), 6.60–6.80 (m, 2H), 7.06 (d, J=8.72 Hz, 2H), 7.54 (t, J=7.20 Hz, 1H), 7.85 (d, J=8.72 Hz, 2H), 8.25 (d, J=3.83 Hz, 1H), 9.90 (s, 1H).

EXAMPLE 1

5-[4-[[1-(Pyridin-2-yl)-(2S)-pyrrolidin-2-yl]methoxy] phenyl methylene]thiazolidine-2,4-dione:

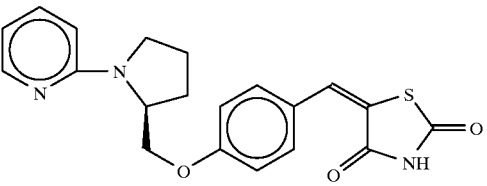

A solution of (S)-4-[[1-(Pyridin-2-yl)pyrrolidin-2-yl] methoxy]benzaldehyde (33.5 g) obtained in preparation 8 and 2,4-thiazolidinedione (16.7 g) in toluene (300 ml) containing piperidine (1.5 g) and benzoic acid (1.8 g) was heated at reflux for 1 h using a Dean Stark water separator. The reaction mixture was cooled and filtered, the filtrate was washed with H$_2$O, dried (Na$_2$SO$_4$) and evaporated under reduced pressure. The crude product was triturated with methanol and filtered to afford 27.5 g (60%) of the title compound mp 164° C.

$[\alpha]_D^{27}$=–73.6 (c. 1.0, DMSO)

$^1$H NMR (CDCl$_3$, 200 MHz): d 2.15 (m, 4H), 3.30 (m, 1H), 3.55 (m, 1H), 3.79 (t, J=9.2 Hz, 1H), 4.35 (dd, J=9.0 and 3.2 Hz, 1H), 4.6 (m, 1H), 6.47 (d, J=8.4 Hz, 1H), 6.65 (t, J=6.8 Hz, 1H), 7.01 (d, J=8.8 Hz, 2H), 7.31 (d, J=8.8 Hz, 2H), 7.48 (s, 1H), 7.56 (t, J=6.0 Hz, 1H), 8.16 (d, J=3.8 Hz, 1H).

EXAMPLE 2

5-[4-[[1-(Pyridin-2-yl)-(2S)-pyrrolidin-2-yl]methoxy] phenyl methyl]thiazolidine-2,4-dione:

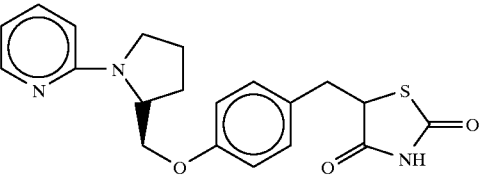

To a stirred suspension of the product obtained in the example 1 (10 g) in methanol (250 ml) at room temperature was added magnesium turnings (10.8 g) and the reaction mixture was stirred at room temperature for 4 hours. The reaction mixture was added to ice water (100 ml), the pH was adjusted to 6.5–7.0 using aqueous hydrochloric acid and the solution was extracted with chloroform (3×150 ml). The combined organic extract was washed with H$_2$O, dried (CaCl$_2$) and the solvent was removed under reduced pressure. The residual mass was chromatographed on silica gel using 0.5% methanol in chloroform to give 6.5 g (65%) of the title compound. mp 79–80° C.

$[\alpha]_D^{27}$=–107.9 (c. 1.0, CHCl$_3$)

$^1$H NMR (CDCl$_3$, 200 MHz): d 2.1 (m, 4H), 3.05 (m, 1H), 3.2–3.6 (m, 3H), 3.82 (t, J=8.8 Hz, 1H). 4.15 (m, 1H), 4.45 (m, 2H), 6.44 (d, J=8.6 Hz, 2H), 6.56 (t, J=6.0 Hz, 1H), 6.9 (d, J=8.4 Hz, 2H), 7.15 (d, J=8.4 Hz, 2H), 7.46 (m,1H), 8.14 (d, J=2.4 Hz, 1H).

EXAMPLE 3

5-[4-[[1-(Pyridin-2-yl)piperidin-4-yloxy]phenyl methylene]thiazolidine-2,4-dione:

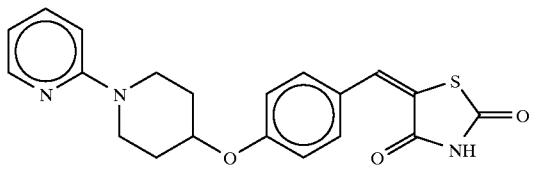

The title compound (1.5 g, 74%) was prepared from 4-[1-(pyridin-2-yl)-4-piperidinyloxy]benzaldehyde (1.5 g), obtained in preparation 9, by a similar procedure to that described in example 1. mp 218–220° C.

$^1$H NMR (CDCl$_3$+DMSO-d$_6$, 200 MHz): d 1.9 (m, 2H), 2.1 (m, 2H), 3.5 (m, 2H), 3.9 (m, 2H), 4.65 (m, 1H), 6.62 (t, J=5.9 Hz, 1H), 6.72 (d, J=8.6 Hz, 1H), 7.02 (d, J=8.4 Hz, 2H), 7.5 (m, 3H), 7.74 (s, 1H), 8.18 (d, J=4.0 Hz, 1H).

EXAMPLE 4

5-[4-[[1-(Pyridin-2-yl)piperidin-4-yl]methoxylphenyl methylene]thiazolidine-2,4-dione:

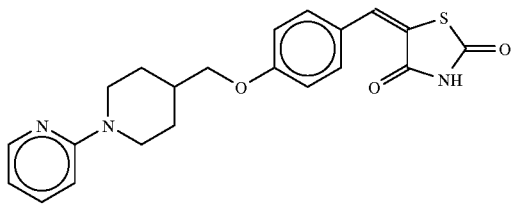

The title compound (0.46 g, 63%) was prepared from 4-[[1-(pyridin-2-yl)piperidin-4-yl]methoxy]benzaldehyde (0.55 g) obtained in preparation 10 by a similar procedure to that described in example 1. mp 233.4° C.

$^1$H NMR (CDCl$_3$, 200 MHz): d 1.45 (m, 2H), 1.9–2.2 (m, 3H), 2.9 (t, J=11.7 Hz, 2H), 3.9 (d, J=6.2 Hz, 2H), 4.38 (approx. d, J=13.0 Hz, 2H), 6.61 (t, J=5.8 Hz, 1H), 6.71 (d, J=8.6 Hz, 1H), 6.99 (d, J=8.8 Hz, 2H), 7.5 (m, 3H), 7.75 (s, 1H), 8.18 (d, J=3.8 Hz, 1H).

EXAMPLE 5

5-[4-[2-[4-(Pyridin-2-yl)piperazin-1-yl]ethoxy]phenyl methylene]thiazolidine-2,4-dione:

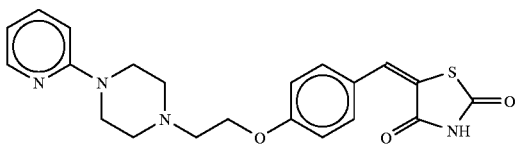

The title compound (0.85 g 64%) was prepared from 4-[2-[4-(pyridin-2-yl)piperazin-1-yl]ethoxy]benzaldehyde (1.0 g), obtained in preparation 11, by a similar procedure to that described in example 1. mp 158–160° C.

$^1$H NMR (CDCl$_3$+DMSO-d$_6$ 200 MHz): d 2.88 (m, 4H), 2.98 (m, 2H), 3.65 (m, 4H), 4.25 (m, 2H), 6.67 (m, 2H), 6.92 (d, J=8.4 Hz, 2H), 7.33 (d, J=8.6 Hz, 2H), 7.48 (m, 2H), 8.2 (d, J=3.6 Hz, 1H).

EXAMPLE 6

5-[4-[[1-(Pyridin-2-yl)-(2S)-pyrrolidin-2-yl]methoxy] phenyl methylene]thiazolidine-2,4-dione, maleic acid salt:

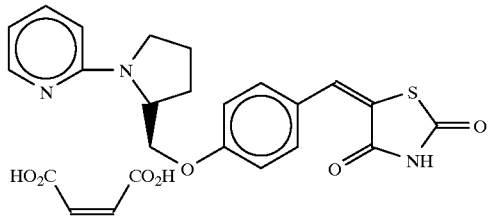

A solution of the product (50 g) obtained in example 1 and maleic acid (16.7 g) in dry acetone (2 L) was stirred at room temperature for 20 h. At the end of this time, the resulting solid was filtered, washed with cold acetone (2×200 ml) and dried under reduced pressure to get 52 g (80%) of the title compound. mp 132° C.

$[\alpha]_D^{27}$=−77.3 (c. 1.0, DMSO)

$^1$H NMR (CDCl$_3$+DMSO-d$_6$, 200 MHz): d 2.13 (bs, 4H), 3.34 (m, 1H), 3.56 (m, 1H), 4.05 (m, 1H), 4.28 (dd, J=9.6 and 3.8 Hz, 1H), 4.53 (bs, 1H), 6.25 (s, 2H), 6.76 (m, 2H), 7.19 (d, J=8.8 Hz, 2H), 7.59 (d, J=8.8 Hz, 2H), 7.72 (m, 1H), 7.79 (s, 1H), 8.13 (d, J=4.2 Hz, 1H), 12.6 (bs, exchangeable with D$_2$O, 1H)

EXAMPLE 7

5-[4-[[1-(Pyridin-2-yl)-(2S)-pyrrolidin-2-yl]methoxy] phenyl methylene]thiazolidine-2,4-dione, hydrochloride salt:

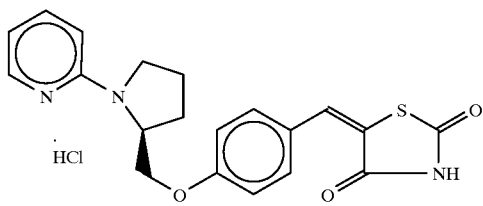

To a solution of the product (40 g) obtained in example 1 in dry acetone (2 L) was bubbled dry HCl gas at 0° C. for 30 min. The resulting solid was filtered, washed with cold acetone (2×200 ml) and dried under reduced pressure to get 33 g (78%) of the title compound as a white solid. mp : 241–243° C.

$[\alpha]_D^{27}$=−131.9 (c. 1.0, DMSO)

$^1$H NMR (DMSO-d$_6$, 200 MHz): d 2.1 (m, 4H), 3.5 (m, 1H), 3.8 (m, 1H), 4.19 (d. J=5.4 Hz, 2H), 4.8 (m, 1H), 6.95 (t, J=6.4 Hz, 1H), 7.06 (d, J 8.4 Hz, 2H), 7.29 (d, J=9.0 Hz, 1H), 7.54 (d, J=8.8 Hz, 2H), 7.74 (s, 1H), 8.0 (m, 2H), 12.6 (bs, exchangeable with D$_2$O, 1H), 14.0 (bs, exchangeable with-D$_2$O, 1H).

EXAMPLE 8

5-[4-[[1-(Pyridin-2-yl)-(2S)-pyrrolidin-2-yl]methoxy]phenyl methylene]thiazolidine-2,4-dione, sodium salt:

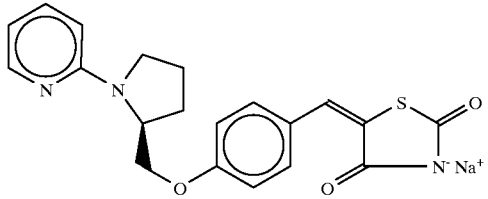

To a solution of 5-[[4-[1-(pyridin-2-yl)-(2S)-pyrrolidin-2-yl]methoxy]phenyl methylene]thiazolidine-2,4-dione (1 g) obtained in example 1 in MeOH (10 ml), at room temperature, NaOMe in MeOH [prepared in situ by dissolving Na (66 mg) in MeOH (5 ml)] was added. The reaction mixture was stirred at room temperature for 1 h and then diluted with Et2O (10 ml). The resulting solid was filtered and dried over $P_2O_5$ under reduced pressure to get 400 mg (38%) of the title product as a white solid. mp : 254–256° C.

$[\alpha]_D^{27} = -85.2$ (c. 1.0, DMSO)

$^1$H NMR (DMSO-$d_6$, 200 MHz): d 2.0 (m, 4H), 3.2 (m, 1H), 3.5 (m, 1H), 3.88 (t, J=8.8 Hz, 1H), 4.21 (dd, J=9.2 and 3.0 Hz, 1H), 4.4 (bs, 1H), 6.55 (m, 2H), 7.06 (d, J=8.8 Hz, 2H), 7.24 (s, 1H), 7.5 (m, 3H), 8.11 (d, J=4.0 Hz, 1H).

EXAMPLE 9

5-[4-[[1-(Pyridin-2-yl)-(2S)-pyrrolidin-2-yl]methoxy]phenyl methyl]thiazolidine-2,4-dione, maleic acid salt:

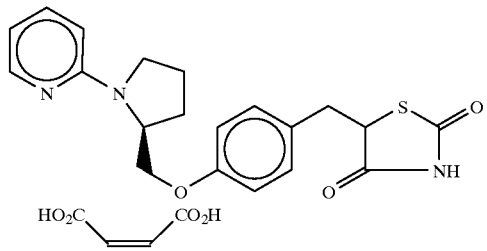

The title compound (2 g, 76%) was prepared as a white solid from 5-[4-[[1-(pyridin-2-yl)-(2S)-pyrrolidin-2-ylmethoxy]phenyl methyl]thiazolidine-2,4-dione (2 g) obtained in example 2 by an analogous procedure to that described in example 6. mp: 58–60° C.

$[\alpha]_D^{27} = -80.5$ (c. 1.27, DMSO)

$^1$H NMR (CDCl$_3$, 200 MHz): d 2.25 (m, 4H), 3.05–3.4 (m, 2H), 3.6 (m, 1H), 3.8 (m, 1H), 4.1 (m, 2H), 4.5 (m, 1H), 4.7 (m, 1H), 6.3 (s, 2H), 6.7–7.0 (m, 4H), 7.12 (d, J=8.4 Hz, 2H), 7.69 (t, J=7.4 Hz, 1H), 8.23 (d, J=4.4 Hz, 1H).

EXAMPLE 10

5-[4-[[1-(Pyridin-2-yl)-(2S)-pyrrolidin-2-yl]methoxy]phenyl methyl]thiazolidine-2,4-dione, sodium salt:

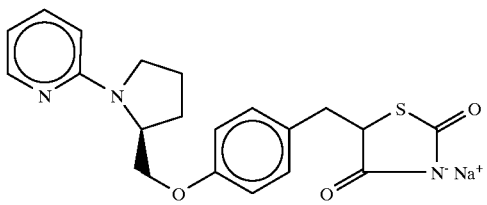

The title compound (0.7 g, 25%) was prepared as a white solid from 5-[4-[[1-(pyridin-2-yl)-(2S)-pyrrolidin-2-yl]methoxy]phenyl methyl]thiazolidine-2,4-dione (2.7 g) obtained in example 2 by an analogous procedure to that described in example 8. mp : 260–262° C.

$[\alpha]_D^{27} = -63.0$ (c. 0.5, DMSO)

$^1$H NMR (DMSO-$d_6$, 200 MHz): d 2.05 (m, 4H), 2.45–2.7 (m, 2H), 3.25 (m, 1H), 3.5 (m, 1H), 3.8 (t, J=8.8 Hz, 1H), 4.1 (m, 2H), 4.4 (bs, 1H), 6.55 (m, 2H), 6.89 (d, J=8.4 Hz, 2H), 7.1 (d, J=8.4 Hz, 2H), 7.5 (m, 1H), 8.12 (d, J=3.8 Hz, 1H).

EXAMPLE 11

5-[4-[[1-(Quinolin-2-yl)-(2S)-pyrrolidin-2-yl]methoxy]phenyl methylene]thiazolidine-2,4-dione:

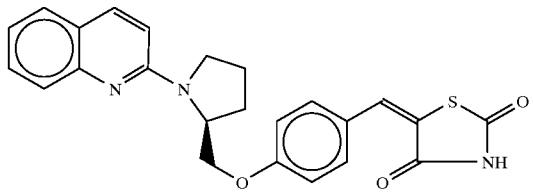

The title compound (2 g, 100%) was prepared as a pale yellow solid from 4-[[1-(quinolin-2-yl)-(2S)-pyrrolidin-2-yl]methoxy]benzaldehyde (1.5 g) obtained in preparation 13, by a similar procedure to that described in example 1. mp : 260–262° C.

$[\alpha]_D^{27} = +49.2$ (c. 1.0, DMSO)

$^1$H NMR (CDCl$_3$, 200 MHz): δ 2.15 (m, 4H), 3.45 (m, 1H), 3.7 (m, 1H), 4.0 (t, J=9.2 Hz, 1H), 4.58 (dd, J=10.0 and 2.9 Hz, 1H), 4.8 (m, 1H), 6.78 (d, J=8.8 Hz, 1H), 7.15–8.0 (complex, 10 H).

EXAMPLE 12

5-[4-[[1-(Quinolin-2-yl)-(2S)-pyrrolidin-2-yl]methoxy]phenyl methyl]thiazolidine-2,4-dione:

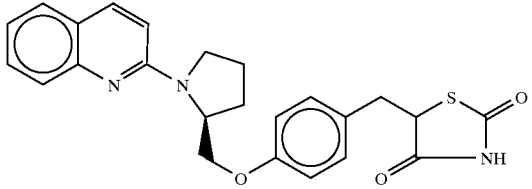

A mixture of ethyl 2-bromo-3-[4-[[1-(quinolin-2-yl)-(2S)-pyrrolidin-2-yl]methoxy]phenyl]propanoate (2.5 g), obtained in preparation 16, thiourea (0.76 g), NaOAc (0.82 g) and EtOH (25 ml) was stirred under reflux for 4 h and extracted with EtOAc, dried (Na$_2$SO$_4$) and concentrated to get 2-imino-5-[4-[[1-(quinolin-2-yl)-(2S)-pyrrolidin-2-yl]methoxy]benzyl]-4-thiazolidinone which was used in the next step without further purification.

A mixture of the above product, 2 N HCl (15 ml) and EtOH (30 ml) was stirred under reflux for 12 h. The reaction mixture was concentrated in vacuo. The residue was diluted with water, neutralized with saturated aqueous NaHCO$_3$ and extracted with ethyl acetate. EtOAc extract was washed with brine, dried (Na$_2$SO$_4$) and concentrated in vacuo. The residue was chromatographed on silica gel with 0–10% MeOH in CHCl$_3$ as eluent to afford the title compound (1.6 g, 68%) as a pale yellow solid. mp: 81–83° C.

$[\alpha]_D^{27}$=−13.8 (c. 1.0, DMSO)

$^1$H NMR (CDCl$_3$, 200 MHz): d 2.1 (m, 4H), 3.1 (dd, J=14.0 and 10.0 Hz, 1H), 3.5 (m, 2H), 3.69 (t, J=8.0 Hz, 1H), 3.9 (t, J=9.2 Hz, 1H), 4.5 (m, 2H), 4.75 (bs, 1H), 6.78 (d, J=9.2 Hz, 1H), 7.2 (m, 5H), 7.6 (m, 2H), 7.73 (d, J=8.4 Hz, 1H), 7.87 (d, J=8.8 Hz, 1H).

EXAMPLE 13

5-[4-[[1-(Quinolin-2-yl)-(2S)-pyrrolidin-2-yl]methoxy]phenyl methyl]thiazolidine-2,4-dione, maleic acid salt:

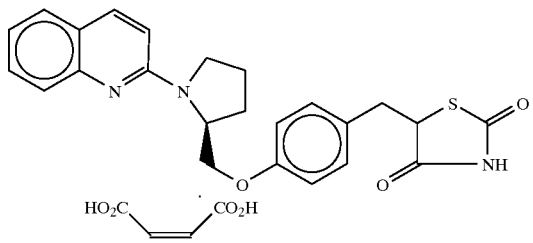

The title compound (0.85 g, 70%) was prepared as an yellow solid from 5-[4-[[1-(quinolin-2-yl)-(2S)-pyrrolidin-2-yl]methoxy]phenyl methyl]thiazolidine-2,4-dione (1.0 g) obtained in example 12, by an analogous procedure to that described in example 6. mp : 84–86° C.

$[\alpha]_D^{27}$=−45.8 (c. 1.0, DMSO)

$^1$H NMR (CDCl$_3$, 200 MHz): d 2.3 (m, 4H), 3.0–3.4 (m, 2H), 3.6–4.3 (m, 4H), 4.41 (dd, J=8.0 and 4.0 Hz, 1H), 5.0 (bs, 1H), 6.33 (s, 2H), 6.8 (m, 2H), 7.1 (m, 3H), 7.5 (m, 1H), 7.75 (m, 2H), 8.2 (d, J=9.4 Hz, 2H).

EXAMPLE 14

5-[4-[[1-(Quinolin-2-yl)-(2S)-pyrrolidin-2-yl]methoxy]phenyl methyl]thiazolidine-2,4-dione, hydrochloride salt:

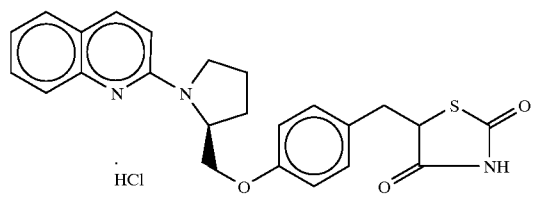

The title compound (0.9 g, 83%) was prepared as an yellow solid from 5-[4-[[1-(quinolin-2-yl)-(2S)-pyrrolidine-2-yl]methoxy]phenyl methyl]thiazolidine-2,4-dione (1.0 g) obtained in example 12, by an analogous procedure to that described in example 7. mp: 144–146° C.

$[\alpha]_D^{27}$=−100.6 (c. 1.0, DMSO)

$^1$H NMR (DMSO-d$_6$, 200 MHz): d 2.1 (m, 4H), 2.9–4.3 (complex, 7 H), 4.9 (m, 1H), 6.83 (d, J 8.0 Hz, 2H), 7.13 (d, J=8.6 Hz, 2H), 7.52 (m, 2H), 7.9 (m, 1H), 7.96 (d, J=7.6 Hz, 1H), 8.21 (d, J=8.0 Hz, 1H), 8.44 (d, J=9.6 Hz, 1H).

EXAMPLE 15

5-[4-[[1-(Quinolin-2-yl)-(2S)-pyrrolidin-2-yl]methoxy]phenyl methyl]thiazolidine-2,4-dione, sodium salt:

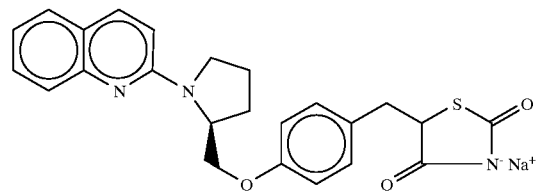

The title compound (0.27 g, 72%) was prepared as a pale yellow solid from 5-[4-[[1-(quinolin-2-yl)-(2S)-pyrrolidin-2-yl]methoxy]phenylmethyl]thiazolidine-2,4-dione (0.36 g) obtained in example 12, by an analogous procedure to that described in example 8. mp : 248–250° C.

$[\alpha]_D^{27}$=+1.4 (c. 1.0, DMSO)

$^1$H NMR (CDCl$_3$, 200 MHz): d 2.1 (m, 4H), 2.5–2.8 (m, 2H), 3.4 (m, 1H), 3.7 (m, 1H), 3.88 (t, J=9.2 Hz, 1H), 4.1 (m, 1H), 4.3 (m, 1H), 4.6 (bs, 1H), 6.9–7.3 (m, 6H), 7.5–7.8 (m, 3H), 8.05 (d, J=9.2 Hz, 1H).

EXAMPLE 16

5-[4-[[1-(Lepidin-2-yl)-(2S)-pyrrolidin-2-yl]methoxy]phenyl methylene]thiazolidine-2,4-dione:

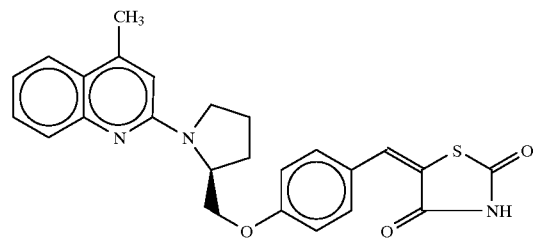

The title compound (1.78 g, 77%) was prepared as a pale yellow solid from 4-[[1-(lepidin-2-yl)-(2S)-pyrrolidin-2-yl]methoxy]benzaldehyde (1.8 g) obtained in preparation 18, by a similar procedure to that described in example 1.

$^1$H NMR (CDCl$_3$+DMSO-d$_6$ 200 MHz): d 2.1 (m, 4H), 2.6 (s, 3H), 3.45 (m, 1H), 3.7 (m, 1H), 3.97 (t, J=9.4 Hz, 1H), 4.55 (dd, J=10.0 and 3.2 Hz, 1H), 4.75 (bs, 1H), 6.65 (s, 1H), 7.2–7.9 (complex, 9H).

EXAMPLE 17

5-[4-[[1-(Lepidin-2-yl)-(2S)-pyrrolidin-2-yl]methoxy]phenyl methyl]thiazolidine-2,4-dione:

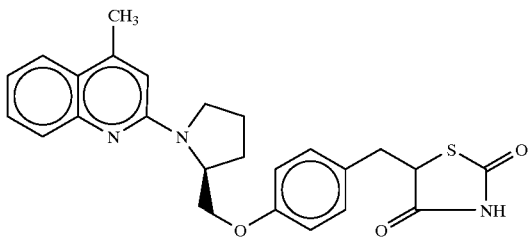

Method A:

A mixture of ethyl 2-chloro-3-[4-[[1-(lepidin-2-yl)-(2S)-pyrrolidin-2-yl]methoxy]phenyl]propanoate (15 g) obtained in preparation 21 and thiourea (5 g) in sulfolane (20 ml) was stirred at 120–130° C. for 4 h under $N_2$ atmosphere. The reaction mixture was cooled to room temperature and 2-methoxyethanol (192 ml), water (50 ml) and conc. HCl (26 ml) were added. The temperature was raised to 80° C. and stirred for 15 h. The reaction mixture was cooled, diluted with EtOAc and washed with aqueous $NH_3$ solution followed by water, dried ($Na_2SO_4$) and concentrated. The crude product was chromatographed on silica gel with 10–40% ethyl acetate in pet ether (gradient elution) as an eluent to afford the title compound (14 g, 95%) as a white solid. mp: 95–97° C.

Method B:

The title compound (0.12 g, 15%) was prepared as a white solid from ethyl 2-bromo-3-[4-[[1-(lepidin-2-yl)-(2S)-pyrrolidin-2-yl]methoxy]phenyl]propanoate (1.5 g), obtained in preparation 22 by an analogous procedure to that described in example 12. mp 95–97° C.

$[\alpha]_D^{27}$=−31.5 (c. 1.0, $CHCl_3$)

$^1$H NMR ($CDCl_3$, 200 MHz): d 2.1 (m, 4H), 2.1 (s, 3H), 3.1 (m, 1H), 3.5 (m, 2H), 3.7 (m, 1H), 3.9 (t, J=9.0 Hz, 1H), 4.5 (m, 2H), 4.75 (bs, 1H), 6.65 (s, 1H), 7.2 (m, 5H), 7.57 (t, J=7.6 Hz, 1H), 7.78 (t, J=8.2 Hz, 2H).

EXAMPLE 18

5-[4-[[1-(Lepidin-2-yl)-(2S)-pyrrolidin-2-yl]methoxy]phenyl methyl]thiazolidine-2,4-dione, maleic acid salt:

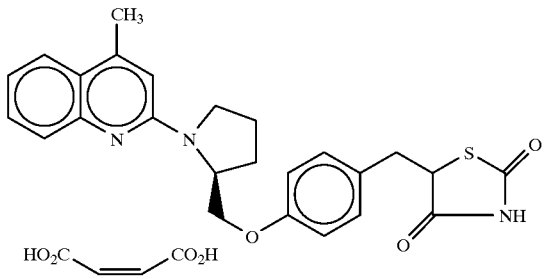

The title compound (0.21 g, 78%) was prepared as a white solid from 5-[4-[[1-(lepidin-2-yl)-(2S)-pyrrolidin-2-yl]methoxy]phenyl methyl]thiazolidine-2,4-dione (0.22 g), obtained in example 17, by an analogous procedure to that described in example 6. mp: 68–70° C.

$[\alpha]_D^{27}$=−72.0 (c. 1.0, DMSO)

$^1$H NMR ($CDCl_3$, 200 MHz): d 2.25 (m, 4H), 2.7 (s, 3H), 3.05–3.45 (m, 2H), 3.8 (m, 1H), 4.0 (m, 1H), 4.2 (m, 2H), 4.48 (dd, J=8.0 and 4.2 Hz, 1H) 5.0 (m, 1H), 6.35 (s, 2H), 6.9 (m, 3H), 7.14 (d, J=8.2 Hz, 2H), 7.44 (t, J=7.6 Hz, 1H), 7.7 (t, J=7.8 Hz, 1H), 7.84 (d, 8.4 Hz, 1H), 8.1 (d, J=8.2 Hz, 1H).

EXAMPLE 19

5-[4-[[1-(Lepidin-2-yl)-(2S)-pyrrolidin-2-yl]methoxy]phenyl methyl]thiazolidine-2,4-dione, hydrochloride salt:

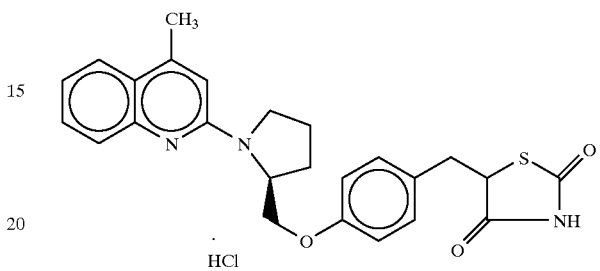

The title compound (0.2 g, 86%) was prepared as a white solid from 5-[4-[[1-(Lepidin-2-yl)-(2S)-pyrrolidin-2-yl]methoxy]phenyl methyl]thiazolidine-2,4-dione (0.22 g) obtained in example 17, by an analogous procedure to that described in example 7. mp: 120° C.

$[\alpha]_D^{27}$=−120.5 (c. 1.0, DMSO)

$^1$H NMR ($CDCl_3$, 200 MHz): d 2.30 (m,4H), 2.7 (s, 3H), 3.0–5.0 (complex, 8H), 6.7–8.0 (complex, 9H), 14.2 (bs, exchangeable with $D_2O$, 1H).

EXAMPLE 20

5-[4-[[1-(Lepidin-2-yl)-(2S)-pyrrolidin-2-yl]methoxy]phenyl methyl]thiazolidine-2,4-dione, sodium salt:

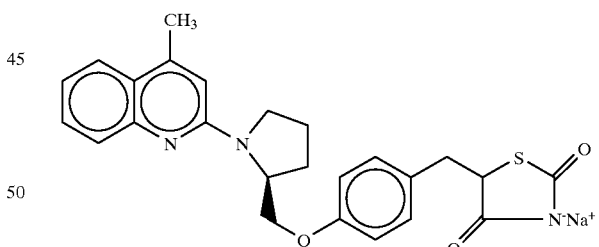

The title compound (0.28 g, 53%) was prepared as a pale yellow solid from 5-[4-[[1-(lepidin-2-yl]-(2S)-pyrrolidin-2-yl]methoxy]phenyl methyl]thiazolidine-2,4-dione (0.5 g) obtained in example 17, by an analogous procedure to that described in example 8. mp : 229° C.

$[\alpha]_D^{27}$=−5.3 (c. 1.0, DMSO)

$^1$H NMR ($CDCl_3$+DMSO-$d_6$): d 2.1 (m, 4H), 2.4–2.7 (m, 5H), 3.4 (m, 1H), 3.65 (m, 1H), 3.85 (m, 1H), 4.1 (m, 1H), 4.3 (m, 1H), 4.6 (bs, 1H), 6.85 (s, 1H), 7.0–7.3 (m, 5H), 7.6 (m, 2H), 7.82 (d, J=8.4 Hz, 1H).

EXAMPLE 21

5-[4-[[1-(Pyridin-2-yl)-(3S)-pyrrolidin-3-yloxy]phenyl methylene]thiazolidine-2,4-dione:

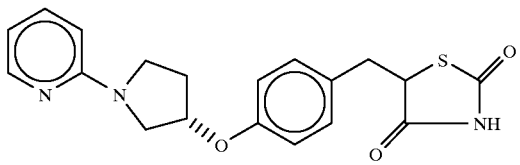

The title compound (0.5 g, 52%) was prepared as a pale yellow solid from 4-[[1-(pyridine-2-yl)-(3S)-pyrrolidin-3-yloxy]benzaldehyde (0.7 g), obtained in preparation 25, by a similar procedure to that described in example 1. mp: 204–206° C.

$[\alpha]_D^{27}$=−20.4 (c. 0.5, DMSO)

$^1$H NMR (CDCl$_3$+DMSO-d$_6$) : d 2.3 (m, 2H), 3.3–3.9 (m, 4H), 5.27 (bs, 1H), 6.5 (m, 2H), 7.14 (d, J=8.2 Hz, 2H), 7.6 (m, 3H), 7.76 (s, 1H), 8.05 (d, J=4.2 Hz, 1H), 12.6 (bs, exchangeable with D$_2$O, 1H).

EXAMPLE 22

5-[4-[[1-(Pyridin-2-yl)-(3S)-pyrrolidin-3-yloxy]phenyl methylene]thiazolidine-2,4-dione, maleic acid salt:

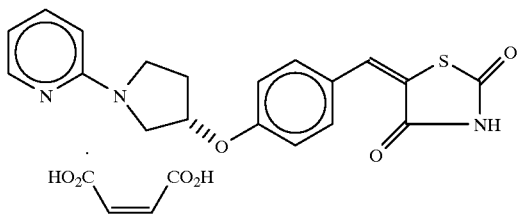

The title compound (0.25 g, 78%) was prepared as a pale yellow solid from 5-[4-[[1-(pyridin-2-yl)-(3S)-pyrrolidin-3-yloxy]phenyl methylene]thiazolidine-2,4-dione (0.25 g), obtained in example 21, by a similar procedure to that described in example 6. mp: 176–178° C.

$[\alpha]_D^{27}$=−15.0 (c. 1.0, DMSO)

$^1$H NMR (CDCl$_3$, 200 MHz): d 2.3 (m, 2H), 4.8 (m, 4H), 5.3 (bs, 1H), 6.2 (s, 2H), 6.7 (m, 2H), 7.17 (d, J=8.6 Hz, 2H), 7.7 (m, 3H), 7.8 (s, 1H), 8.05 (d, J=5 Hz, 1H).

EXAMPLE 23

5-[4-[1-(Pyridin-2-yl)-(3S)-pyrrolidin-3-yloxy]phenyl methylene]thiazolidine-2,4-dione, hydrochloride salt:

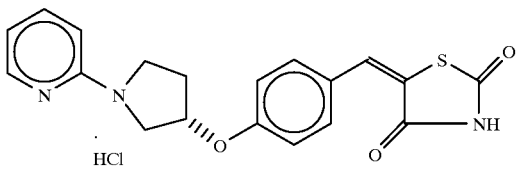

The title compound (0.13 g, 78%) was prepared as a white solid from 5-[4-[[1-(pyridin-2-yl)-(3S)-pyrrolidin-3-yloxy] phenyl methylene]thiazolidine-2,4-dione (0.15 g) obtained in example 21, by an analogous procedure to that described in example 7. mp: 256–258° C.

$[\alpha_D^{27}$=−20.44 (c. 0.45, DMSO)

$^1$H NMR (CDCl$_3$+DMSO-d$_6$): d 2.3 (m, 2H), 3.6–4.0 (m, 4H), 5.4 (bs, 1H), 6.9 (t, J=6.6 Hz, 1H), 7.2 (m, 3H), 7.6 (d, J=8.4 Hz, 2H), 7.78 (s, 1H), 8.0 (m, 2H), 12.6 (bs, exchangeable with D$_2$O, 1H).

EXAMPLE 24

5-[4-[[1-(Pyridin-2-yl)-(3S)-pyrrolidin-3-yloxy]phenyl methyl]thiazolidine-2,4-dione:

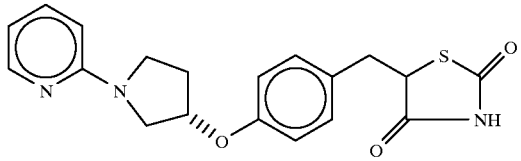

The title compound (0.25 g, 35%) was prepared as a white solid from 5-[4-[[1-(pyridin-2-yl)-(3 S)-pyrrolidin-3-yloxy] phenyl methylene]thiazolidine-2,4-dione (0.7 g) obtained in example 21, by a similar procedure to that described in example 2. mp: 78–80° C.

$^1$H NMR (CDCl$_3$+DMSO-d$_6$): d 2.35 (m, 2H), 3.1 (m, 1H), 3.45 (m, 1H), 3.7 (m, 2H), 3.8 (m, 2H), 4.5 (m, 1H), 5.05 (bs, 1H), 6.39 (d, J=8.6 Hz, 1H), 6.56 (t, J=6.2 Hz, 1H), 6.84 (d, J=8.6 Hz, 2H), 7.15 (d, J=8.4 Hz, 2H), 7.5 (m, 1H), 8.14 (d, J=4.6 Hz, 1H).

EXAMPLE 25

5-[4-[[4-(Pyridin-2-yl)morpholin-2-yl]methoxy]phenyl methylene]thiazolidine-2,4-dione:

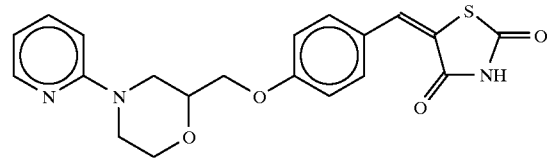

The title compound (19 g, 89%) was prepared as a pale yellow solid from 4-[[4-(pyridin-2-yl)morpholin-2-yl]methoxy]benzaldehyde (16.0 g) obtained from preparation 27 by a similar procedure to that described in example 1, mp 188° C.

$^1$H NMR (CDCl$_3$, 200 MHz): d 2.82–3.18 (m, 2H), 3.70–4.40 (m, 7H), 6.61–6.80 (m, 2H), 7.02 (d, J=8.72 Hz, 2H), 7.41 (d, J=8.72 Hz, 2H), 7.55 (t, J=6.73 Hz, 1H), 7.68 (s, 1H), 8.23 (d, J 3.10 Hz, 1H).

EXAMPLE 26

5-[4-[[4-(Pyridin-2-yl)morpholin-2-yl]methoxy]phenyl methyl]thiazolidine-2,4-dione:

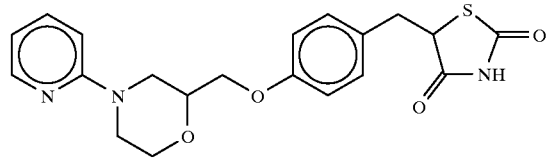

The title compound (5.0 g, 30%) was prepared as a white solid from 5-[4-[[4-(pyridin-2-yl)morpholin-2-yl]methoxy] phenyl methylene]thiazolidine-2,4-dione (17.0 g) obtained in example 25 by a similar procedure to that described in example 2. mp 139–142° C.

$^1$H NMR (CDCl$_3$, 200 MHz): d 2.82–3.18, (m, 2H), 3.11 (dd, J=14.12 and 9.78 Hz, 1H), 3.46 (dd, J=14.12 and 3.73 Hz, 1H), 3.81 (td, J=11.53 and 2.49 Hz, 1H), 3.90–4.35 (m, 6H), 4.48 (dd, J=9.78 and 3.73 Hz, 1H), 6.65–6.75 (m, 2H), 6.91 (d, J=8.63 Hz, 2H), 7.16 (d, J=8.63 Hz, 2H), 7.53 (t, J=6.87 Hz, 1H), 8.22 (d, J=3.41 Hz, 1H),

EXAMPLE 27

5-[4-[[4-(Pyridin-2-yl)morpholin-2yl]methoxy]phenyl methyl]thiazolidine-2,4-dione, sodium salt:

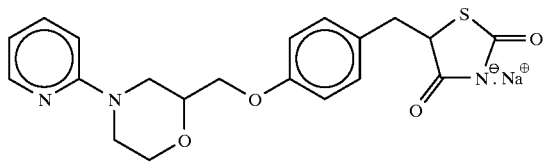

The title compound (2.9 g, 89%) was prepared as a white solid from 5-[4-[[4-(pyridin-2-yl)morpholin-2-yl]methoxy] phenyl methyl]thiazolidine-2,4-dione (3.1 g) obtained in example 25 by an analogous procedure to that described in example 8. mp 272° C.

$^1$H NMR (DMSO-d$_6$, 200 MHz): d 2.51–2.92 (m, 2H), 3.20–3.40 (m, 1H), 3.53–3.72 (m, 1H), 3.74–4.20 (m, 7H), 4.20–4.40 (m, 1H), 6.69 (t, J=5.81 Hz, 1H), 6.86 (d, J=8.62 Hz, 2H), 7.11 (d, J=5.81 Hz, 1H), 7.21 (d, J=8.62 Hz, 2H), 7.57 (t, J=8.3 Hz, 1H), 8.14 (d, J=4.35 Hz, 1H).

Mutation in colonies of laboratory animals and different sensitivities to dietary regimens have made the development of animal models with non-insulin dependent diabetes associated with obesity and insulin resistance possible. Genetic models such as db/db and ob/ob (See Diabetes, (1982) 31(1): 1–6) in mice and fa/fa and zucker rats have been developed by the various laboratories for understanding the pathophysiology of disease and testing the efficacy of new antidiabetic compounds (Diabetes, (1983) 32: 830–838; Annu. Rep. Sankyo Res. Lab. (1994). 46: 1–57). The homozygous animals, C57 BL/KsJ-db/db mice developed by Jackson Laboratory, US, are obese, hyperglycemic, hyperinsulinemic and insulin resistant (J. Clin. Invest., (1990) 85: 962–967), whereas heterozygous are lean and normoglycemic. In db/db model, mice progressively develop insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

The compounds of the present invention showed blood sugar and triglycerides lowering activities through improved insulin resistance. This was demonstrated by the following in vivo experiments.

Male C$_{57}$BL/KsJ-db/db mice of 8 to 14 weeks age, having body weight range of 35 to 60 grams, procured from the Jackson Laboaotory, USA, were used in the experiment. The mice were provided with standard feed (National Institute of Nutrition, Hyderabad, India) and acidified water, ad libitum. The animals having more than 300 mg/dl blood sugar were used for testing. The number of animals in each group was 4.

The random blood sugar and triglyceride levels were measured by collecting blood (100 μl) through orbital sinus, using heparinised capillary in tubes containing EDTA which was centrifuged to obtain plasma. The plasma glucose and triglyceride levels were measured spectrometrically, by glucose oxidase and glycerol-3-PO$_4$ oxidase/peroxidase enzyme (Dr. Reddy's Lab. Diagnostic Division Kits, Hyderabad, India) methods respectively. On 6th day the blood samples were collected one hour after administration of test compounds/vehicle for assessing the biological activity.

Test compounds were suspended on 0.25% carboxymethyl cellulose or water (for water soluble compounds) and administered to test group at a dose of 10 to 30 mg/kg through oral gavage daily for 6 days. The control group received vehicle (dose 10 ml/kg). Troglitazone (100 mg/kg, daily dose) was used as a standard drug which showed 28% reduction in random blood sugar level on 6th day.

The blood sugar and triglycerides lowering activities of the test compound was calculated according to the formula:

$$\text{Blood sugar/triglycerides lowering activity}(\%) = 1 - \frac{DT/DC}{TC/ZC} \times 100$$

ZC=Zero day control group value
DC=Zero day treated group value
TC=Control group value on test day
DT=Treated group value on the test day No adverse effects were observed for any of the mentioned compounds of invention in the above test.

| Compound | Dose (mg/kg) | Reduction in Blood Glucose Level (%) | Triglyceride Lowering (%) |
|---|---|---|---|
| Example 6 | 10 | 49 | 71 |
| Example 7 | 30 | 67 | 43 |
| Example 12 | 30 | 27 | 49 |
| Example 20 | 30 | 30 | 62 |
| Example 23 | 10 | 46 | 10 |
| Example 27 | 10 | 56 | 29 |

The experimental results from the db/db mice suggest that the novel compounds of the present invention also possess therapeutic utility as a prophylactic or regular treatment for obesity, cardiovascular disorders such as hypertension, hyperlipidaemia and other diseases; as it is known from the literature that such diseases are interrelated to each other.

Subacute toxicity in rats:

Groups of 20 rats, consisting of 10 males and 10 females, weighing between 120 to 140 gm, received orally 100 mg/kg of compound of Example 6 for 28 days. The behavioral changes and body weights were monitored daily. The rats were sacrificed on the 29th day and blood was collected for hematological and biochemical estimations. All vital organs were examined both macroscopically and microscopically.

The compound of example 6 at 100 mg/kg dose did not produce any mortality. At the end of 28 days treatment no significant deviations from the control were observed in hematological and biochemical parameters. No gross macroscopic and microscopic changes of heart, lungs, bone marrow, kidneys and spleen were observed.

| Parameters | Control | Example 6 (100 mg/kg) |
|---|---|---|
| Hematology | | |
| Hemoglobin (gm/dl) | 15.18 ± 0.69 | 14.88 ± 0.46 |
| RBC (x $10^6$/mm$^3$) | 7.33 ± 0.75 | 7.08 ± 0.93 |
| WBC (x $10^3$/mm$^3$) | 8.08 ± 2.01 | 9.19 ± 2.11 |
| PVC (%) | 52.06 ± 2.58 | 52.21 ± 2.67 |
| Organ Weight | | |
| Heart (g) | 0.59 ± 0.09 | 0.61 ± 0.08 |

What is claimed is:

1. A compound of formula (I),

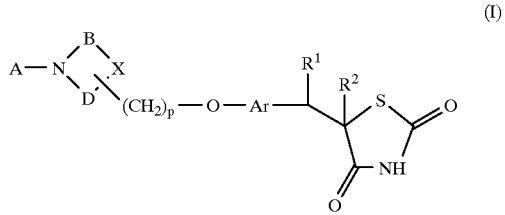

its tautomeric forms, its steroisomers, its polymorphs, its pharmaceutically acceptable salts or its pharmaceutically acceptable solvates, where A represents a single or fused, substituted or unsubstituted carbocyclic aromatic group, a substituted or unsubstituted 5-membered heterocyclic group with one heteroatom selected from oxygen, sulfur or nitrogen, or a substituted or unsubstituted six-membered heterocyclic group with one or more nitrogen atoms B represents a substituted or unsubstituted linking group between N and X and B contains 1–4 carbon atoms; D represents a bond or D represents a substituted or unsubstituted linking group between N and X when D contains 1–4 carbon atoms; with the proviso that when the linking group B, D or both is substituted the substituent is not =O or =S; X represents a $CH_2$ group or a heteroatom selected from nitrogen, oxygen or sulfur; Ar represents substituted or unsubstituted divalent aromatic or heterocyclic group; $R^1$ and $R^2$ are same or different and represent hydrogen, lower alkyl, halogen, alkoxy or hydroxy or $R^1$ and $R^2$ taken together represent a bond and p is an integer ranging from 0 to 4.

2. A compound according to claim 1, wherein A is substituted or unsubstituted six-membered heterocyclic group, single or fused, having one or more oxo group on the ring.

3. A compound according to claim 1, wherein the linking group B between N and X is saturated or contains one or more double bonds.

4. A compound according to claim 1, wherein the linking group D between N and X is saturated or contains one or more double bonds.

5. A compound as claimed in claim 1, wherein the linking group between N and X represented by B and D is saturated or contains 1–2 double bonds.

6. A compound as claimed in claim 1, wherein the heterocycle comprising hydrocarbon linking groups represented by B and D, and N and X is a 3 to 5 membered ring.

7. A compound as claimed in claim 1, wherein the aromatic group represented by A contains 1–2 rings.

8. A compound as claimed in claim 1, wherein A is a five membered heterocyclic group which contains one heteroatom selected from oxygen, nitrogen or sulfur.

9. A compound as claimed in claim 1, wherein A is a substituted aromatic group, a substituted 5-membered heterocyclic group or a 6-membered heterocyclic group, wherein the substituents are selected from hydroxy, amino, halogen, substituted or unsubstituted ($C_1$–$C_{12}$)alkyl, ($C_3$–$C_6$)cycloalkyl, cycloaminoalkyl, aryl, aralkyl, heteroaryl, alkoxy, aryloxy, alkoxycarbonyl, aryloxycarbonyl, amino($C_1$–$C_6$)alkyl, hydroxy($C_1$–$C_6$)alkyl, ($C_1$–$C_6$)alkoxy, thio($C_1$–$C_6$)alkyl, ($C_1$–$C_6$)alkylthio, acyl group, carboxylic acid derivatives, acyloxy or sulfonic acid derivatives.

10. A compound as claimed in claim 9, where the substituents are substituted with halogen, lower alkyl, lower alkoxy, hydroxy or amino groups.

11. A compound as claimed in claim 1, wherein the substituents on the adjacent carbon atoms on the group represented by A form part of a substituted or unsubstituted 4–7 membered cyclic structure which is an aromatic or saturated or unsaturated carbocyclic ring or an aromatic or saturated or unsaturated heterocyclic ring, wherein the hetero atoms are selected from nitrogen, oxygen or sulfur.

12. A compound as claimed in claim 11, wherein the substituents on the cyclic structure are selected from the group that consists of hydroxy, amino, halogen, substituted or unsubstituted ($C_1$–$C_{12}$)alkyl, ($C_3$–$C_6$)cycloalkyl, cycloaminoalkyl, aryl, aralkyl, heteroaryl, alkoxy, aryloxy, alkoxycarbonyl, aryloxycarbonyl, amino($C_1$–$C_6$)alkyl, hydroxy($C_1$–$C_6$)alkyl, ($C_1$–$C_6$)alkoxy, thio ($C_1$–$C_6$)alkyl, ($C_1$–$C_2$)alkylthio, acyl, carboxylic acid derivatives, acyloxy and sulfonic acid derivatives.

13. A compound as claimed in claim 1, wherein the substituents on the linking group represented by B and D are selected from the group consisting of hydroxy, amino, halogen, optionally substituted linear or branched ($C_1$–$C_{12}$) alkyl, ($C_3$–$C_6$)cycloalkyl groups, ($C_1$–$C_6$)alkoxy, ($C_3$–$C_6$) cycloalkoxy, aryl, heterocyclic groups, ($C_2$–$C_6$)acyl, ($C_2$–$C_6$)acyloxy, hydroxyl($C_1$–$C_6$)alkyl, amino($C_1$–$C_6$) alkyl, mono or di($C_1$–$C_6$)alkylamino, cyclo($C_2$–$C_6$) alkylamino groups, two substituents together with the adjacent carbon atoms to which they are attached may form a substituted or unsubstituted 5–7 membered cyclic structure which may be an aromatic or saturated or unsaturated carbocyclic ring or an aromatic or saturated or unsaturated heterocyclic-ring wherein the hetero atoms are selected from N, O or S and the substituents on said cyclic structure are selected from the group consisting of hydroxy, amino, halogen, substituted or unsubstituted ($C_1$–$C_{12}$)alkyl group, ($C_3$–$C_6$)cycloalkyl group, cycloaminoalkyl groups, aryl group, aralkyl, heteroaryl-group, alkoxy, aryloxy, alkoxycarbonyl, aryloxycarbonyl, amino($C_1$–$C_6$)alkyl, hydroxy($C_1$–$C_6$)alkyl, ($C_1$–$C_6$)alkoxy, thio($C_1$–$C_6$)alkyl, ($C_1$–$C_6$)alkylthio, acyl group, carboxylic acid derivatives, acyloxy group, and sulfonic acid derivatives.

14. A process for the preparation of thiazolidinedione derivatives of formula (1) as defined in claim 1, their tautomeric forms, their stereoisomers, their polymorphs, their pharmaceutically acceptable salts or their pharmaceutically acceptable solvates which comprises:

a) reacting a compound of formula (V)

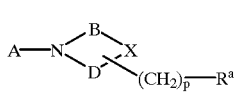

where A, B, D, X and p are as defined in claim 1, and $R^a$ is a hydroxy group with a compound of general formula (VI)

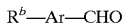 (VI)

where Ar is as defined in claim 1, and $R^b$ is a hydroxy group or a halide group to yield a compound of formula (VII)

(VII)

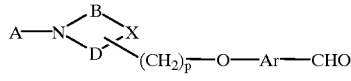

where A, B, D, X, Ar and p are as defined earlier; and b) reacting a compound of formula (VII) obtained in step (a) with 2,4-thiazolidinedione to yield a compound of formula (VIII)

(VIII)

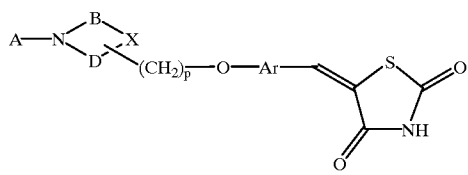

where A, B, D, X, Ar, and p are as defined earlier.

15. The process according to claim 14, further comprising:

reducing the compound of formula (VIII) obtained in step (b) of claim 14, by known methods, to obtain the compound of formula (IX)

(IX)

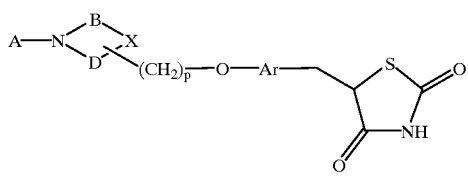

where A, B, D, X, Ar and p are as defined in claim 14.

16. The process according to claim 14, further comprising resolving the compound of formula (VIII) into its stereoisomers.

17. The process according to claim 15, further comprising resolving the compound of formula (IX) into its steroisomers.

18. A process for the preparation of thiazolidinedione derivatives of formula (I) as defined in claim 1, their tautomeric forms, their stereoisomers, their polymorphs, their pharmaceutically acceptable salts or their pharmaceutically acceptable solvates which comprises reacting a compound of formula (V)

(V)

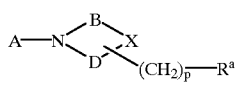

where A, B, D, X and p are as defined in claim 1, and $R^a$ is a hydroxy group, or a compound of formula (X)

(X)

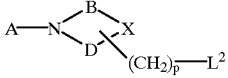

where A, B, D, X, and p are as defined in claim 1, and $L^2$ is a leaving group, with a compound of formula (XIII)

(XIII)

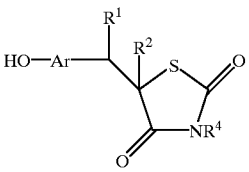

where $R^1$, $R^2$ and Ar are as defined in claim 1, and $R^4$ is hydrogen or a nitrogen protecting group.

19. A process for the preparation of thiazolidinedione derivatives of formula (I) as defined in claim 1, their tautomeric forms, their stereoisomers, their polymorphs, their pharmaceutically acceptable salts or their pharmaceutically acceptable solvates which comprises:

a) reacting a compound of formula (V)

(V)

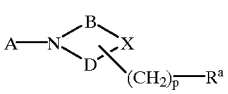

where A, B, D, X and p are as defined in claim 1 and $R^a$ is a hydroxy group or a compound of formula (X)

(X)

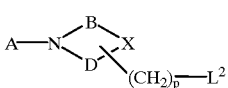

where A, B, D, X, and p are as defined in claim 1, and $L^2$ is a leaving group, with a compound of formula (XX)

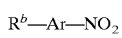 (XX)

where $R^b$ is a halogen atom or a hydroxy group and Ar is as defined in claim 1, to yield a compound of formula (XIX)

(XIX)

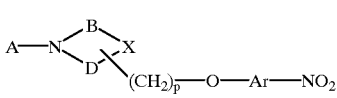

where all symbols are as defined in claim 1;

b) reducing compound of formula (XIX) obtained in step (a) above by to obtain a compound of formula (XVIII)

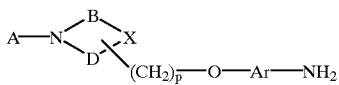

(XVIII)

where all symbols are as defined in claim 1;

c) diazotization of compound of formula (XVIII) followed by treatment with acrylic acid esters/hydrohalo acids to obtain a compound of formula (XVII)

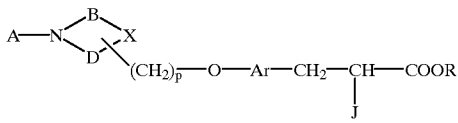

(XVII)

where A, B, D, X, p and Ar are as defined in claim 1, J is a halogen atom and R is a lower alkyl group, with thiourea followed by treatment with an acid; and d) reacting compound of formula (XVII) obtained in step (c) above with thiourea followed by treatment with acid to obtain compound of formula (I) defined in claim 1, where $R^1$ and $R^2$ both represent hydrogen atoms.

20. A process for the preparation of intermediate (VII),

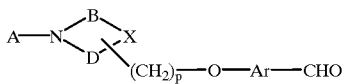

(VII)

where A, B, D, X, Ar and p are as in claim 1, which comprises:

a) reacting a compound of formula (XI)

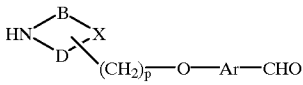

(XI)

where B, D, X, Ar and p are as defined above, with a compound of formula (III)

A—L¹ (III)

where A is as defined above and $L^1$ is a leaving group or b) reacting a compound of formula (X),

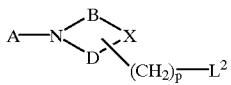

(X)

where A, B, D, X and p are as defined above and $L^2$ is a leaving group, with a compound of formula (VI)

$R^b$—Ar—CHO (VI)

where Ar is as defined above and $R^b$ is a hydroxy group.

21. A pharmaceutical composition useful for the treatment and/or prophylaxis of diseases in which insulin resistance is the underlying pathophysiological mechanism such as type II diabetes, impaired glucose tolerance, dyslipidaemia, hypertension, coronary heart disease and other cardiovascular disorders including atherosclerosis, insulin resistance associated with obesity and psoriasis, for treating diabetic complications and other diseases such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia, which comprises a compound of the general formula (I) as defined in claim 1, together with pharmaceutically acceptable carriers, diluents, or solvates.

22. Compounds according to claim 1, which are selected from the the group consisting of:

5-[4-[[1-(Pyridin-2-yl)-(2S)-pyrrolidin-2-yl]methoxy]phenyl methylene]thiazolidine-2,4-dione;

5-[4-[[1-(Pyridin-2-yl)-(2R)-pyrrolidin-2-yl]methoxy]phenyl methylene]thiazolidine-2,4-dione;

5-[4-[[1-(Pyridin-2-yl)-(2S)-pyrrolidin-2-yl]methoxy]phenyl methyl]thiazolidine-2,4-dione;

5-[4-[[1-(Pyridin-2-yl)-(2R)-pyrrolidin-2-yl]methoxy]phenyl methyl]thiazolidine-2,4-dione;

5-[4-[[1-(Pyridin-2-yl)piperidin-4-yloxy]phenyl methylene]thiazolidine-2,4-dione;

5-[4-[[1-(Pyridin-2-yl)piperidin-4-yl]methoxy]phenyl methylene]thiazolidine-2,4-dione;

5-[4-[2-[4-(Pyridin-2-yl)piperazin-1-yl]ethoxy]phenyl methylene]thiazolidine-2,4-dione;

5-[4-[[1-(Pyridin-2-yl)-(2S)-pyrrolidin-2-yl]methoxy]phenyl methylene]thiazolidine-2,4-dione, maleic acid salt;

5-[4-[[1-(Pyridin-2-yl)-(2R)-pyrrolidin-2-yl]methoxy]phenyl methylene]thiazolidine-2,4-dione, maleic acid salt;

5-[4-[[1-(Pyridin-2-yl)-(2S)-pyrrolidin-2-yl]methoxy]phenyl methylene]thiazolidine-2,4-dione, hydrochloride salt;

5-[4-[[1-(Pyridin-2-yl)-(2R)-pyrrolidin-2-yl]methoxy]phenyl methylene]thiazolidine-2,4-dione, hydrochloride salt;

5-[4-[[1-(Pyridin-2-yl)-(2S)-pyrrolidin-2-yl]methoxylpheny]methylene]thiazolidine-2,4-dione, sodium salt;

5-[4-[[1-(Pyridin-2-yl)-(2R)-pyrrolidin-2-yl]methoxy]phenyl methylene]thiazolidine-2,4-dione, sodium salt;

5-[4-[[1-(Pyridin-2-yl)-(2S)-pyrrolidin-2-yl]methoxy]phenyl methyl]thiazolidine-2,4-dione, maleic acid salt;

5-[4-[[1-(Pyridin-2-yl)-(2R)-pyrrolidin-2-yl]methoxy]phenyl methyl]thiazolidine-2,4-dione, maleic acid salt;

5-[4-[[1-(Pyridin-2-yl)-(2S)-pyrrolidin-2-yl]methoxy]phenyl methyl]thiazolidine-2,4-dione, sodium salt;

5-[4-[[1-(Pyridin-2-yl)-(2R)-pyrrolidin-2-yl]methoxy]phenyl methyl]thiazolidine-2,4-dione, sodium salt;

5-[4-[[1-(Quinolin-2-yl)-(2S)-pyrrolidin-2-yl]methoxy]phenyl methylene]thiazolidine-2,4-dione;

5-[4-[[1-(Quinolin-2-yl)-(2R)-pyrrolidin-2-yl]methoxy]phenyl methylene]thiazolidine-2,4-dione;

5-[4-[[1-(Quinolin-2-yl)-(2S)-pyrrolidin-2-yl]methoxy]phenyl methyl]thiazolidine-2,4-dione;

5-[4-[[1-(Quinolin-2-yl)-(2R)-pyrrolidin-2-yl]methoxy]phenyl methyl]thiazolidine-2,4-dione;

5-[4-[[1-(Quinolin-2-yl)-(2S)-pyrrolidin-2-yl]methoxy] phenyl methyl]thiazolidine-2,4-dione, maleic acid salt;

5-[4-[[1-(Quinolin-2-yl)-(2R)-pyrrolidin-2-yl]methoxy] phenyl methyl]thiazolidine-2,4-dione, maleic acid salt;

5-[4-[[1-(Quinolin-2-yl)-(2S)-pyrrolidin-2-yl]methoxy] phenyl methyl]thiazolidine-2,4-dione, hydrochloride;

5-[4-[[1-(Quinolin-2-yl)-(2R)-pyrrolidin-2-yl]methoxy] phenyl methyl]thiazolidine-2,4-dione, hydrochloride;

5-[4-[[1-(Quinolin-2-yl)-(2S)-pyrrolidin-2-yl]methoxy] phenyl methyl]thiazolidine-2,4-dione, sodium salt;

5-[4-[[1-(Quinolin-2-yl)-(2R)-pyrrolidin-2-yl]methoxy] phenyl methyl]thiazolidine-2,4-dione, sodium salt;

5-[4-[[1-(Lepidin-2-yl)-(2S)-pyrrolidin-2-yl]methoxy] phenyl methylene]thiazolidine-2,4-dione;

5-[4-[[1-(Lepidin-2-yl)-(2R)-pyrrolidin-2-yl]methoxy] phenyl methylene]thiazolidine-2,4-dione;

5-[4-[[1-(Lepidin-2-yl)-(2S)-pyrrolidin-2-yl]methoxy] phenyl methyl]thiazolidine-2,4-dione;

5-[4-[[1-(Lepidin-2-yl)-(2R)-pyrrolidin-2-yl]methoxy] phenyl methyl]thiazolidine-2,4-dione;

5-[4-[[1-(Lepidin-2-yl)-(2S)-pyrrolidin-2-yl]methoxy] phenyl methyl]thiazolidine-2,4-dione, maleic acid salt;

5-[4-[[1-(Lepidin-2-yl)-(2R)-pyrrolidin-2-yl]methoxy] phenyl methyl]thiazolidine-2,4-dione, maleic acid salt;

5-[4-[[1-(Lepidin-2-yl)-(2S)-pyrrolidin-2-yl]methoxy] phenyl methyl]thiazolidine-2,4-dione, hydrochloride salt;

5-[4-[[1-(Lepidin-2-yl)-(2R)-pyrrolidin-2-yl]methoxy] phenyl methyl]thiazolidine-2,4-dione, hydrochloride salt;

5-[4-[[1-(Lepidin-2-yl)-(2S)-pyrrolidin-2-yl]methoxy] phenyl methyl]thiazolidine-2,4-dione, sodium salt;

5-[4-[[1-(Lepidin-2-yl)-(2R)-pyrrolidin-2-yl]methoxy] phenyl methyl]thiazolidine-2,4-dione, sodium salt;

5-[4-[[1-(Pyridin-2-yl)pyrrolidin-3-yloxy]phenyl methylene]thiazolidine-2,4-dione;

5-[4-[[1-(Pyridin-2-yl)-(3S)-pyrrolidin-3-yloxy]phenyl methylene]thiazolidine-2,4-dione and its salts;

5-[4-[[1-(Pyridin-2-yl)-(3R)-pyrrolidin-3-yloxy]phenyl methylene]thiazolidine-2,4-dione and its salts;

5-[4-[[1-(Pyridin-2-yl)pyrrolidin-3-yloxy]phenyl methylene]thiazolidine-2,4-dione, maleic acid salt;

5-[4-[[1-(Pyridin-2-yl)pyrrolidin-3-yloxy]phenyl methylene]thiazolidine-2,4-dione, hydrochloride salt;

5-[4-[[1-(Pyridin-2-yl)pyrrolidin-3-yloxy]phenyl methyl] thiazolidine-2,4-dione;

5-[4-[[1-(Pyridin-2-yl)-(3S)-pyrrolidin-3-yloxy]phenyl methyl]thiazolidine-2,4-dione and its salts;

5-[4-[[1-(Pyridin-2-yl)-(3R)-pyrrolidin-3-yloxy]phenyl methyl]thiazolidine-2,4-dione and its salts;

5-[4-[[4-(Pyridin-2-yl)morpholin-2-yl]methoxy]phenyl methylene]thiazolidine-2,4-dione and its salts;

5-[4-[[4-(Pyridin-2-yl)-(2S)-morpholin-2-yl]methoxy] phenyl methylene]thiazolidine-2,4-dione and its salts;

5-[4-[[4-(Pyridin-2-yl)-(2R)-morpholin-2-yl]methoxy] phenyl methylene]thiazolidine-2,4-dione and its salts;

5-[4-[[4-(Pyridin-2-yl)morpholin-2-yl]methoxy]phenyl methyl]thiazolidine-2,4-dione and its salts;

5-[4-[[4-(Pyridin-2-yl)-(2S)-morpholin-2-yl]methoxy] phenyl methyl]thiazolidine-2,4-dione and its salts;

5-[4-[[4-(Pyridin-2-yl)-(2R)-morpholin-2-yl]methoxy] phenyl methyl]thiazolidine-2,4-dione;

5-[4-[[4-(Pyridin-2-yl)morpholin-2yl]methoxy]phenyl methyl]thiazolidine-2,4-dione, sodium salt;

5-[4-[[4-(Pyridin-2-yl)-(2S)-morpholin-2yl]methoxy] phenyl methyl]thiazolidine-2,4-dione, sodium salt;

5-[4-[[4-(Pyridin-2-yl)-(2R)-morpholin-2yl]methoxy] phenyl methyl]thiazolidine-2,4-dione, sodium salt;

5-[4-[[4-(Pyridin-2-yl)aziridin-2-yl]methoxy]phenyl methylene]thiazolidine-2,4-dione;

5-[4-[[4-(Pyridin-2-yl)-(2S)-aziridin-2-yl]methoxy] phenyl methylene]thiazolidine-2,4-dione;

5-[4-[[4-(Pyridin-2-yl)-(2R)-aziridin-2-yl]methoxy] phenyl methylene]thiazolidine-2,4-dione;

5-[4-[[4-(Pyridin-2-yl)aziridin-2-yl]methoxy]phenyl methyl]thiazolidine-2,4-dione;

5-[4-[[4-(Pyridin-2-yl)-(2S)-aziridin-2-yl]methoxy] phenyl methyl]thiazolidine-2,4-dione;

5-[4-[[4-(Pyridin-2-yl)-(2R)-aziridin-2-yl]methoxy] phenyl methyl]thiazolidine-2,4-dione;

5-[4-[[4-(Quinolin-2-yl)aziridin-2-yl]methoxy]phenyl methylene]thiazolidine-2,4-dione;

5-[4-[[4-(Quinolin-2-yl)-(2S)-aziridin-2-yl]methoxy] phenyl methylene]thiazolidine-2,4-dione;

5-[4-[[4-(Quinolin-2-yl)-(2R)-aziridin-2-yl]methoxy] phenyl methylene]thiazolidine-2,4-dione;

5-[4-[[4-(Quinolin-2-yl)aziridin-2-yl]methoxy]phenyl methyl]thiazolidine-2,4-dione;

5-[4-[[4-(Quinolin-2-yl)-(2S)-aziridin-2-yl]methoxy] phenyl methyl]thiazolidine-2,4-dione; and 5-[4-[[4-(Quinolin-2-yl)-(2R)-aziridin-2-yl]methoxy] phenyl methyl]thiazolidine-2,4-dione.

23. A pharmaceutical composition as claimed in claim 21, in the form of a tablet, capsule, powder, syrup, solution, or suspension.

24. A method of preventing or treating diseases in which insulin resistance is the underlying pathophysiological mechanism comprising administering a compound of formula (I) as defined in claim 1, and a pharmaceutically acceptable carrier, diluent or solvate to a patient in need thereof.

25. A pharmaceutical composition which comprises a compound according to claim 22, as an effective ingredient and a pharmaceutically acceptable carrier, diluent or excipient.

26. A method of reducing blood glucose, triglycerides and free fatty acids comprising a compound of formula (1), as defined in claim 1 and a pharmaceutically acceptable carrier, diluent or solvates.

27. A method according to claim 24, wherein the disease is type II diabetes, impaired glucose tolerance, dyslipidaemia, hypertension, coronary heart disease, a cardiovascular disorder, atherosclerosis, insulin resistance associated with obesity and psoriasis, diabetic complications, polycystic ovarian syndrome (PCOS), renal diseases including diabetic nephropathy, glomerulonephritis, glomerular sclerosis, nephrotic syndrome, hypertensive nephrosclerosis, end-stage renal diseases, microalbuminuria, or eating disorders or dementia.

* * * * *